United States Patent
Knoblich et al.

(10) Patent No.: US 11,884,933 B2
(45) Date of Patent: Jan. 30, 2024

(54) SUPPORTED IN VITRO DEVELOPED TISSUE CULTURE AND CULTURING METHODS

(71) Applicant: IMBA—INSTITUT FÜR MOLEKULARE BIOTECHNOLOGIE GMBH, Vienna (AT)

(72) Inventors: Jürgen Knoblich, Mödling (AT); Madeline A. Lancaster, Cambridge (GB)

(73) Assignee: IMBA—INSTITUT FÜR MOLEKULARE BIOTECHNOLOGIE GMBH, Vienna (AT)

( * ) Notice: Subject to any disclaimer, the term of this patent is extended or adjusted under 35 U.S.C. 154(b) by 120 days.

(21) Appl. No.: 16/067,797

(22) PCT Filed: Jan. 11, 2017

(86) PCT No.: PCT/EP2017/050469
§ 371 (c)(1),
(2) Date: Jul. 2, 2018

(87) PCT Pub. No.: WO2017/121754
PCT Pub. Date: Jul. 20, 2017

(65) Prior Publication Data
US 2019/0017016 A1   Jan. 17, 2019

(30) Foreign Application Priority Data
Jan. 11, 2016 (EP) .................................... 16150783

(51) Int. Cl.
*C12N 5/0793* (2010.01)
*C12N 5/074* (2010.01)
*C12N 5/0735* (2010.01)
*C12N 5/071* (2010.01)
*G01N 33/50* (2006.01)

(52) U.S. Cl.
CPC ......... *C12N 5/0619* (2013.01); *C12N 5/0606* (2013.01); *C12N 5/0696* (2013.01); *C12N 5/0697* (2013.01); *G01N 33/5058* (2013.01); C12N 2500/38 (2013.01); C12N 2501/115 (2013.01); C12N 2501/33 (2013.01); C12N 2501/385 (2013.01); C12N 2501/415 (2013.01); C12N 2501/727 (2013.01); C12N 2501/999 (2013.01); C12N 2506/02 (2013.01); C12N 2506/45 (2013.01); C12N 2513/00 (2013.01); C12N 2527/00 (2013.01); C12N 2531/00 (2013.01); C12N 2533/40 (2013.01); C12N 2533/52 (2013.01); C12N 2533/90 (2013.01); C12N 2535/10 (2013.01)

(58) Field of Classification Search
CPC .......... C12N 2500/38; C12N 2501/115; C12N 2501/33; C12N 2501/385; C12N 2501/415; C12N 2501/727; C12N 2501/999; C12N 2506/02; C12N 2506/45; C12N 2513/00; C12N 2527/00; C12N 2531/00; C12N 2533/40; C12N 2533/52; C12N 2533/90; C12N 2535/10; C12N 5/0606; C12N 5/0619; C12N 5/0696; C12N 5/0697; G01N 33/5058
See application file for complete search history.

(56) References Cited

U.S. PATENT DOCUMENTS

| | | |
|---|---|---|
| 4,829,000 A | 5/1989 | Kleinman et al. |
| 8,067,237 B2 | 11/2011 | Mooney et al. |
| 2003/0091979 A1 | 5/2003 | Eschenhagen |
| 2003/0232430 A1 | 12/2003 | Cibelli et al. |
| 2005/0124003 A1 | 6/2005 | Atala et al. |
| 2006/0263336 A1 | 11/2006 | Caplan |
| 2009/0239298 A1 | 9/2009 | Gerecht et al. |
| 2010/0196923 A1 | 8/2010 | Atala |
| 2011/0142433 A1 | 6/2011 | Oh et al. |
| 2012/0009157 A1 | 1/2012 | Okano et al. |
| 2013/0236503 A1 | 9/2013 | Levenberg et al. |
| 2013/0280319 A1 | 10/2013 | Mathiowitz et al. |
| 2015/0330970 A1 | 11/2015 | Knoblich et al. |

OTHER PUBLICATIONS

Carson et al. The FASEB Journal 26(8) pp. 3240-3242, (2012).*
International Search Report from International Patent Application No. PCT/EP2017/050469, dated Jun. 16, 2017.
Chung et al., "Human Embryonic Stem Cell Lines Generated Without Embryo Destruction," Cell Stem Cell (2008), 2(2), pp. 113-117.
Eiraku et al., "Mouse Embryonic Stem Cell Culture for Generation of Three-Dimensional Retinal and Cortical Tissues," Nature Protocols (2012), 7(1), pp. 69-79.
Han et al., "Microribbon-Like Elastomers for Fabricating Macroporous and Highly Flexible Scaffolds that Support Cell Proliferation in 3D," Advanced Functional Materials (2012), 23(3), pp. 1-13.
Kadoshima et al., "Self-Organization of Axial Polarity, Inside-Out Layer Pattern, and Species-Specific Progenitor Dynamics in Human ES Cell-Derived Neocortex," PNAS (2013), 110(50), pp. 20284-20289.

(Continued)

*Primary Examiner* — Blaine Lankford
(74) *Attorney, Agent, or Firm* — Greer, Burns & Crain, Ltd

(57) ABSTRACT

An elongated or fiber-supported multicellular aggregation of multipotent cells, wherein multipotent cells are arranged in an oblong or longish arrangement with an aspect ratio of a prolate dimension to a perpendicular dimension of at least 2:1, or supported by a fibrous structure, and wherein the aggregate contains cells at different stages of differentiation, and the aggregate contains polar cells; methods of generating such aggregates; methods of developing the aggregates further into tissue organoids and kits for such methods.

25 Claims, 23 Drawing Sheets

(56) References Cited

OTHER PUBLICATIONS

Lancaster et al., "Cerebral Organoids Model Human Brain Development and Microcephaly," Nature (2013), vol. 501, pp. 373-379.
Paşca et al., "Functional Cortical Neurons and Astrocytes from Human Pluripotent Stem Cells in 3D Culture," Nature Methods (2015), vol. 12, pp. 1-8.
Xia et al., "Differentiation of Neuroepithelia from Human Embryonic Stem Cells," Methods in Molecular Biology (2009), vol. 549, pp. 51-58.
Yin et al., "Engineering Stem Cell Organoids," Cell Stem Cell (2016), 18(1), pp. 25-38.

* cited by examiner

Fig. 8
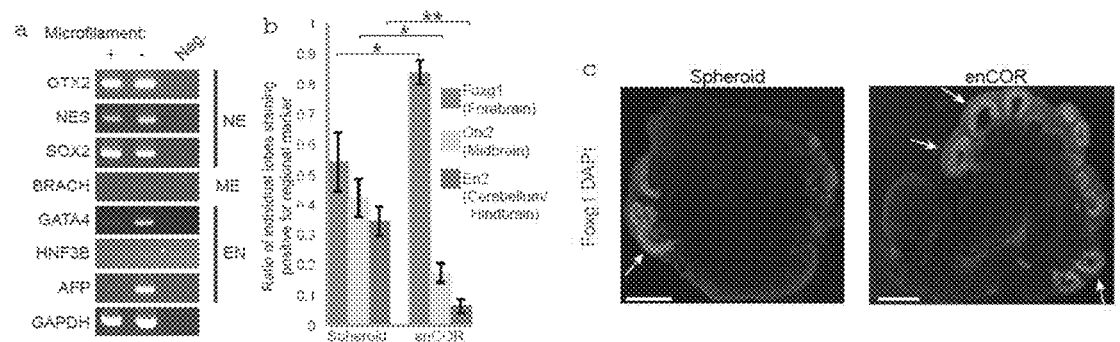
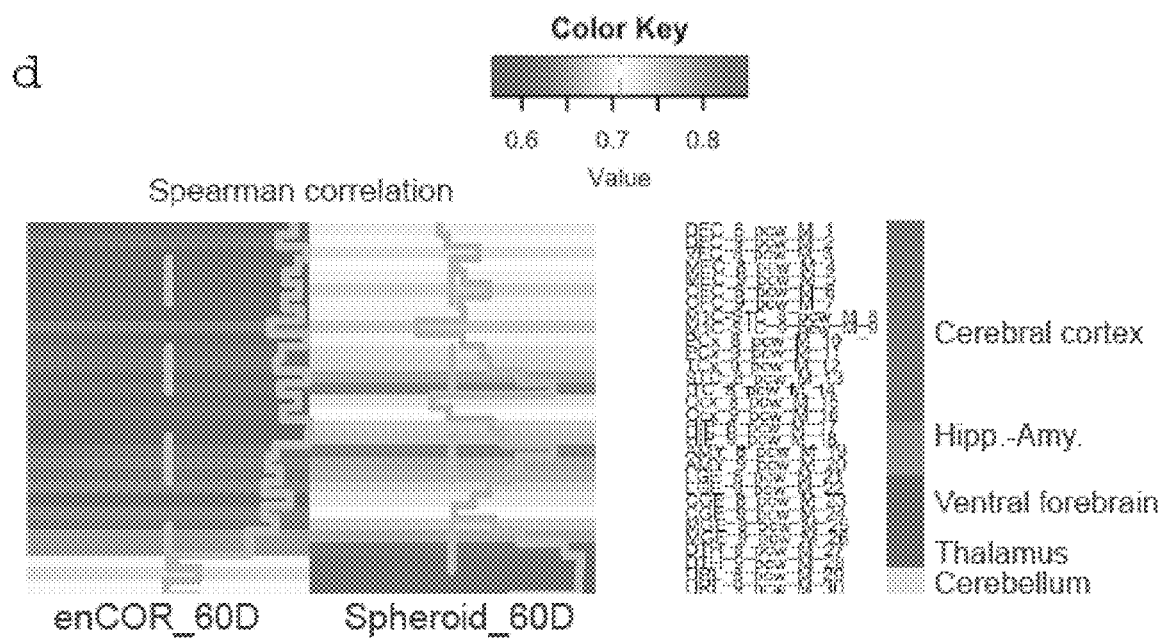

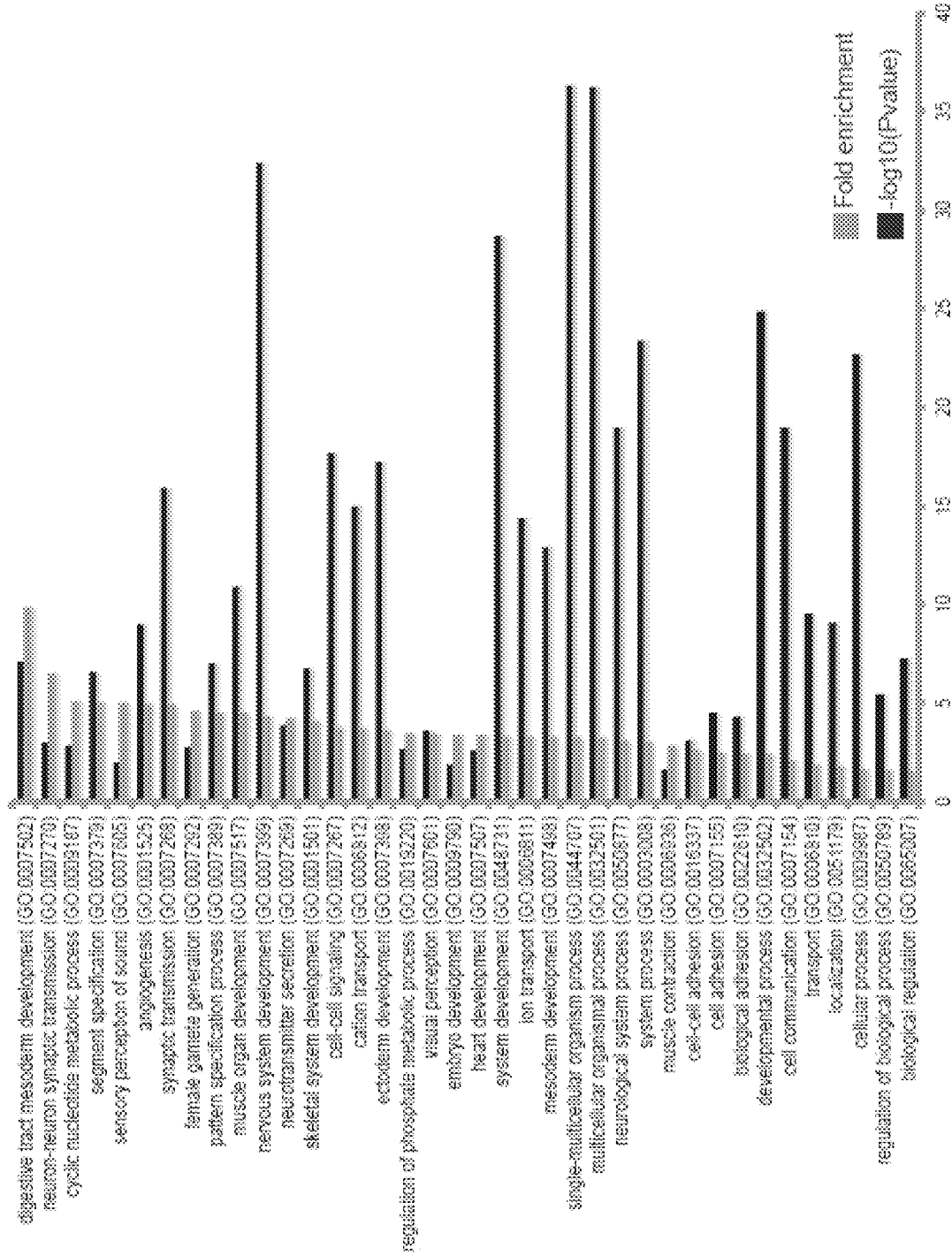
Cont. Fig. 16a

Cont. Fig. 17
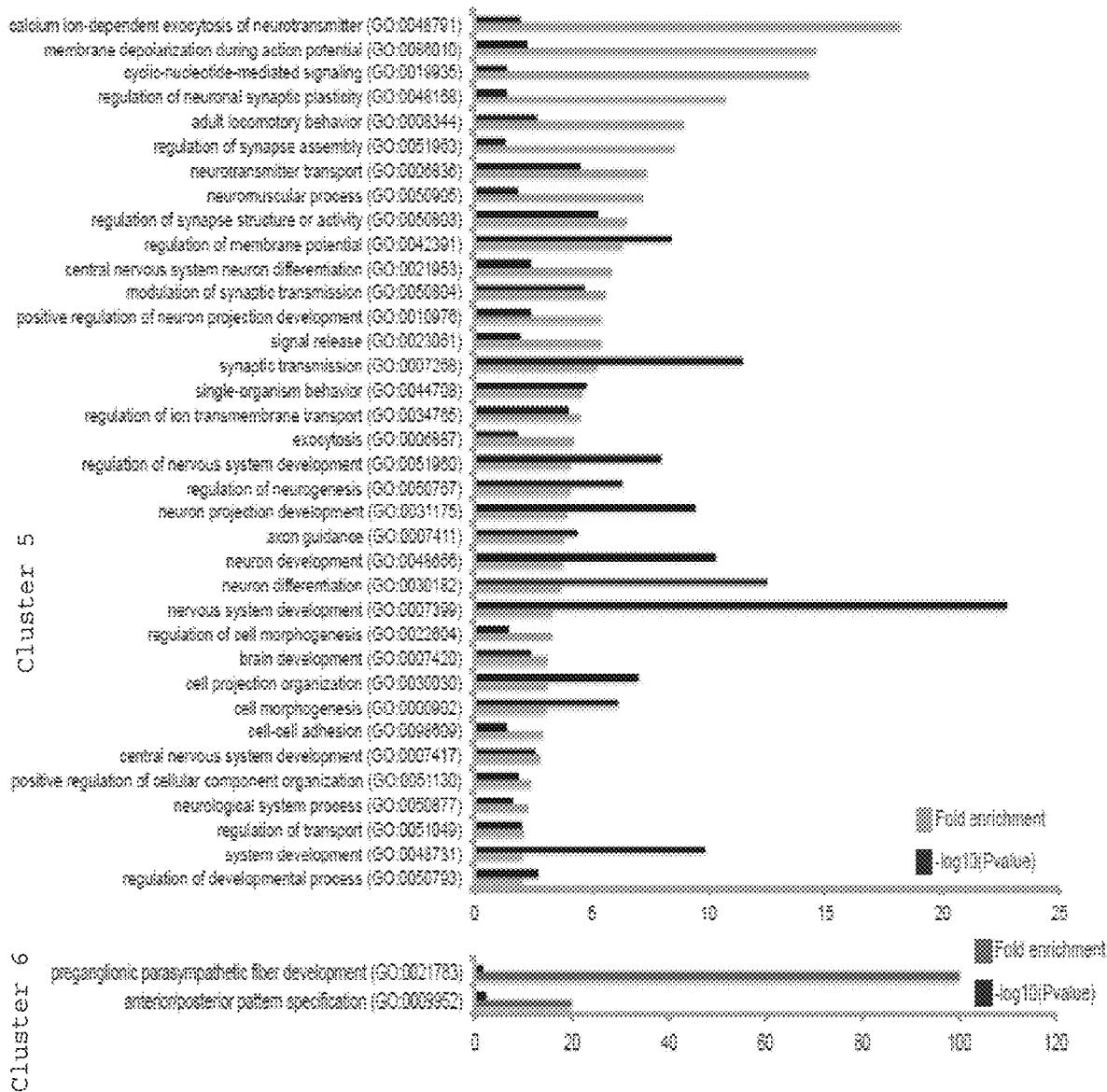

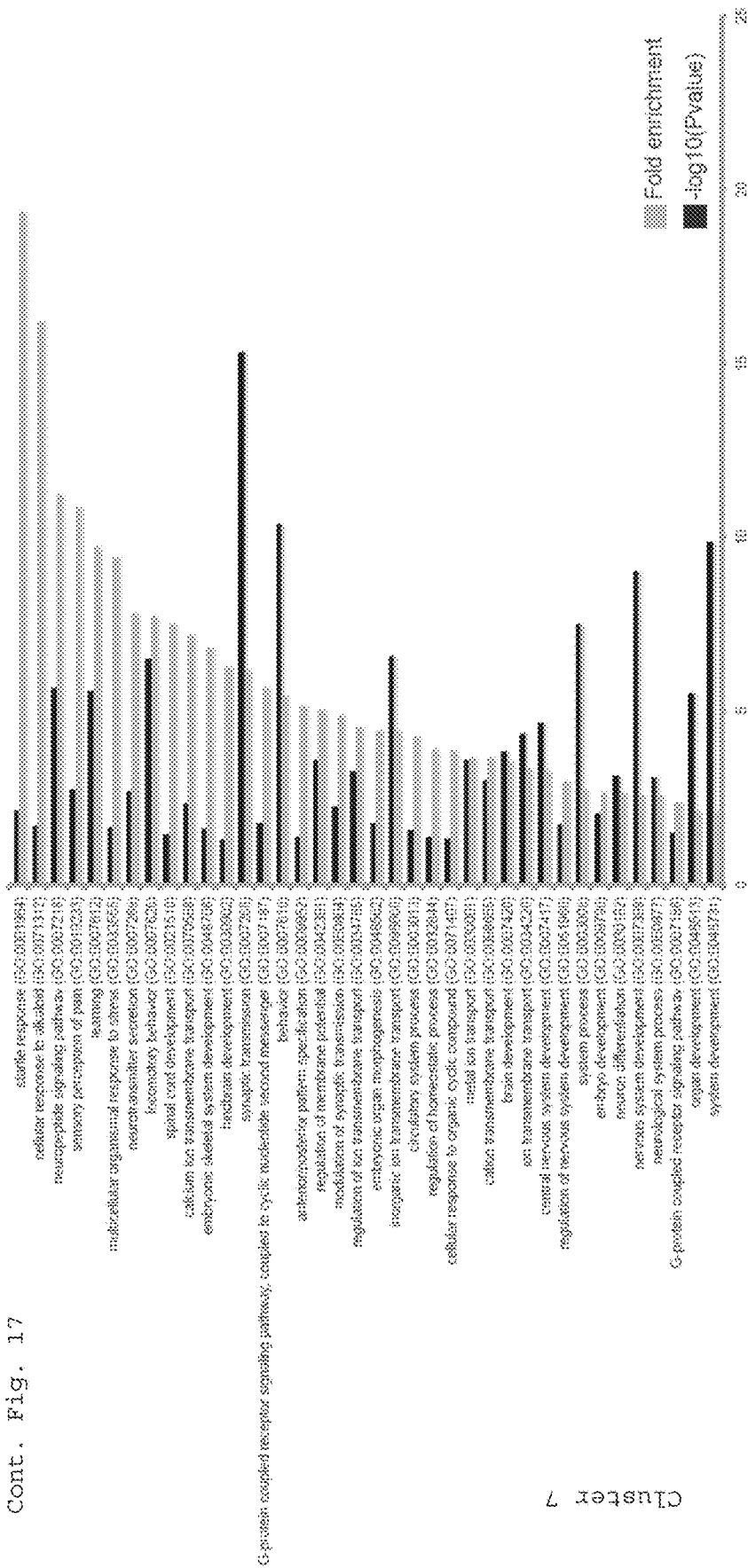
Cont. Fig. 17

Fig. 18
a
Pluripotent markers:
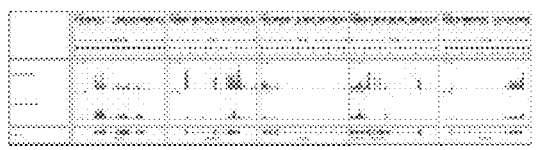
Neuroectodermal markers:
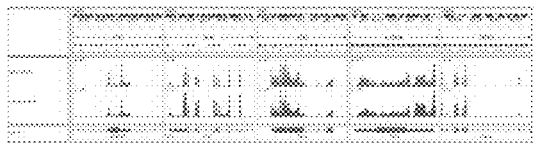
Mesendodermal markers:
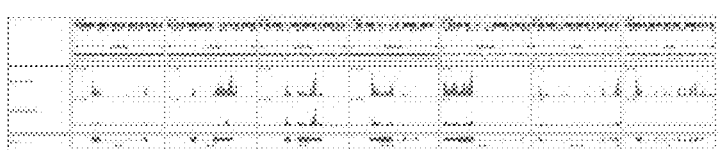
b
Rostral-Caudal patterning markers:
Dorsal-Ventral Forebrain patterning markers:
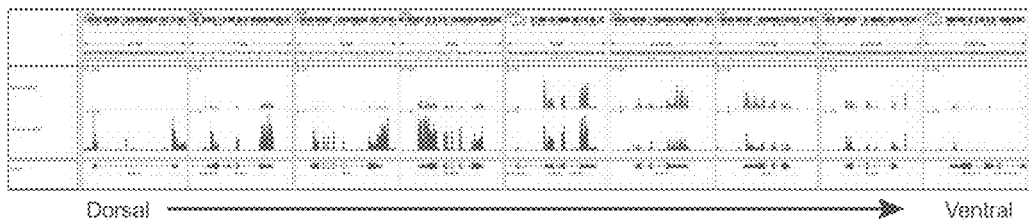
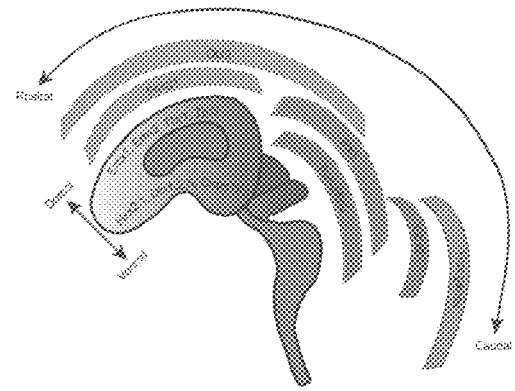
c
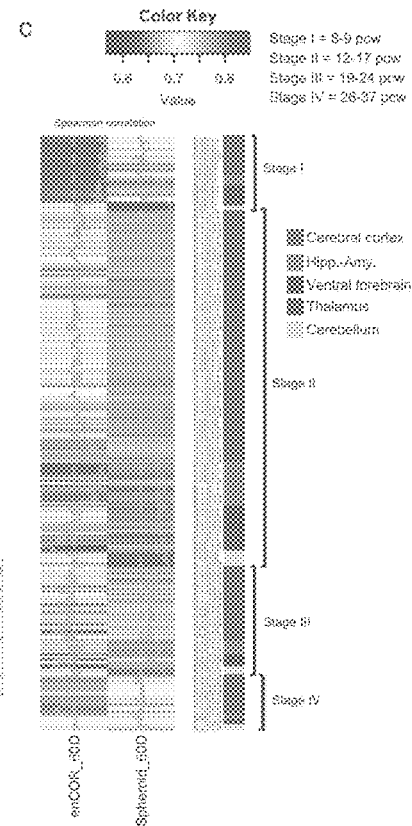

SUPPORTED IN VITRO DEVELOPED TISSUE CULTURE AND CULTURING METHODS

BACKGROUND

The present invention relates to the field of in vitro cell cultures to model organ behaviour as found in vivo.

Three-dimensional cultures of developing tissues in vitro, called organoids, are emerging as powerful tools in the study of development, homeostasis and disease in a variety of tissue types. Organoids have been generated for a number of epithelia such as intestine, liver, kidney and inner ear. Central nervous system organoids have also been described with methods to generate individual brain regions such as cerebellum, retina, and cerebral cortex. WO 2014/090993 A1 and Lancaster et al., Nature 501 (7467) (2013): 373-379 describe whole brain organoids, called cerebral organoids, that display a variety of different brain regions and features of spatial and temporal patterning that mimic that seen in vivo.

A precursory step to organoid development is usually the formation of embryoid bodies (EBs). A method of generating embryoid bodies is described by Xia and Zhang. 2009 (Methods Mol Biol (2009) 549: 51-8), however not for generating diversely differentiated organoids but to obtain neural rosettes. As described by Xia and Zhang, floating embryoid bodies are grown from embryoid stem cells (ESC) in a well plate in ESC growth medium. WO 2006/021950 describes the formation of embryoid bodies by culturing undifferentiated embryonic stem cells on a porous three dimensional scaffold. Porous 3D scaffolds, like sponges are known, e.g. from US 2013/02365503 for cell culture growth, here to grow already differentiated cells, in particular olfactory bulb cells and endothelial cells, or from WO 2007/070660 for controlled recruitment or release of cells. A method of differentiating embryoid bodies with selected media is disclosed in WO 2010/090007 A1. US 2011/143433 A2 describes microcarriers with extracellular matrix materials for propagating stem cells. Cells were grown on DE53 cellulose material, on which the cells adhere to and grow bulbously or spherically (FIG. 168). US 2013/280319 A1 relates to kits with wet spun polymeric microstructures for microencapsulation and filament spinning.

Organoid technologies are proving useful not only for developmental studies, but also for examining disease states. For example, intestinal organoids have provided important insight into mechanisms underlying the gastrointestinal symptoms seen in cystic fibrosis. Similarly, neural organoids have now been used to model and examine mechanisms of specific neurological diseases, namely microcephaly and autism with macrocephaly. These studies highlight the power of this approach to examine pathogenic mechanisms of disorders that have proven difficult to study in model organisms.

Although organoids hold enormous potential for modelling a wide variety of syndromes, their in vitro nature predisposes these systems to high variability. Depending upon the feature in question, this variability can be minute or quite significant. For example, the rate of generation of organoids with an intestinal identity will be consistent when starting with adult intestinal stem cells. However, when starting with human pluripotent stem cells (hPSCs) one can expect a greater degree of variability as other identities can leak into the system due to the pluripotent nature of the starting cell population. Nonetheless, the heterogeneity produced also tends to better recapitulate the cellular diversity of the organ as a whole. Thus, one must balance reproducibility with heterogeneity depending on the question at hand.

Along these lines, the existence of variability in morphology between different preparations of brain organoids has been described (WO 2014/090993; Lancaster et al. 2013, supra). This batch-to-batch variability can be addressed by carefully selecting preparations with optimal morphologies at various key stages and performing a series of quality control checks before analyses are performed. Such an approach has proven adequate for the study of neurological diseases with more severe phenotypes, such as severe microcephaly. However, subtle phenotypes can be more difficult to reliably identify if the range of variability of the feature in question is high. For example, less severe size defects may be difficult to detect.

Furthermore, although existing 3D methods for cortical differentiation nicely recapitulate progenitor zone organization and temporal patterning, neuronal organization may still show differences to that seen in vivo. Specifically, some previous organoids show no or little radialized cortical plate formation and therefore have no or little development of distinct cortical neuron layers. A lack of an organized cortical plate makes the study of neuronal migration disorders such as lissencephaly and certain heterotopias more difficult.

It is therefore a goal of the present invention to improve organoids, in particular to increase consistent developmental potential.

SUMMARY

The present invention provides a method of generating an elongated or fiber-supported multicellular aggregation of multipotent cells comprising the steps of
a) providing a plurality of pluripotent or non-human totipotent cells that are located in an oblong or longish arrangement and/or are located on a fibrous support,
b) letting said cells grow and differentiate in said arrangement, wherein said cells form intercellular attachments and adhere to each other; and an elongated or fiber-supported multicellular aggregation of multipotent cells obtainable by such a method.

Also provided is an elongated or fiber-supported multicellular aggregation of multipotent cells wherein multipotent cells are arranged in an oblong or longish arrangement with an aspect ratio of a prolate dimension to a perpendicular dimension of at least 2:1, or on a fibrous support, and wherein said aggregate contains cells at different stages of differentiation, and said aggregate contains polar cells. The polar cells may have a uniform orientation with respect to the center of said aggregate. Preferably said polar cells constitute at least 50% of the cells of the aggregate.

An aspect of the invention is a method of generating an artificial tissue culture comprising
o) providing an elongated or fiber-supported multicellular aggregation of multipotent cells,
p) culturing said elongated or fiber-supported multicellular aggregation in a three dimensional matrix, wherein said cells are allowed to differentiate, thereby expanding said cells, and
q) culturing said expanded cells of step p) in a suspension culture.

Within the concept of this aspect, the invention also provides method of generating an artificial tissue culture comprising u) providing multicellular aggregation of multipotent cells,
v) culturing said multicellular aggregation in a three dimensional matrix, preferably a gel, wherein said cells are allowed to differentiate, thereby expanding said cells,
w) culturing said expanded cells of step v) in a suspension culture, and
r) adding dissolved material of a three dimensional matrix to said suspension culture, whereby the dissolved material adheres to the culture and forms a matrix.

The invention also relates to an artificial tissue culture obtainable by any such method.

In particular provided is an artificial neuronal tissue culture comprising a radially organized cortical plate. Such a culture may be in vitro grown from an aggregate of cells. The culture is in particular not a culture of an in vivo developed brain or a tissue sample thereof.

The invention also provides the use of the inventive cell culturing methods and cell aggregates and tissues in methods of investigating genes and drugs for effects in altering tissue culture. Genes may be up- or downregulated for this purpose. Drugs can be added to the culture during any stage, preferably stages b) and o)-q) or u) to w) optionally also r). By this method, developmental disorders influenced by (defective) genes or by harmful (e.g. teratogenic) drugs or compounds can be investigated.

The invention further provides a kit comprising i) a solid support of rod-shaped or lattice-shaped or fibrous structure, and ii) a three-dimensional matrix. The three-dimensional matrix is preferably a gel and/or an extracellular matrix or any component thereof selected from collagen, laminin, entactin, and heparin-sulfated proteoglycan or any combination thereof. i) and ii) are different components.

Also provided is a kit comprising vitamin C; vitamin A, 2-mercaptoethanol; bFGF; ROCK inhibitor; insulin; a GSK3beta inhibitor; a Wnt activator, preferably CHIR 99021; an antibacterial agent, preferably Penicillin and/or Streptomycin; a SMAD inhibitor, preferably dorsomorphin and/or SB-431542; a retinoid, preferably retinoic acid; or any combination thereof. The kit may further comprise i) and/or ii). Preferably a compound is included in the kit that is both a GSK3beta inhibitor and a Wnt activator, preferably CHIR 99021. A preferred kit of the invention comprises the rod-shaped or lattice-shaped or fibrous structure with a combined GSK3beta inhibitor and a Wnt activator, such as CHIR 99021.

All embodiments of the invention are described together in the following detailed description and all preferred embodiments relate to all embodiments, aspects, methods, cultures and aggregates and kits alike. E.g. descriptions of aggregates and cultures as such also read on the cells used in the inventive methods. Kits or their components can be used in or be suitable for inventive methods. Any component used in the described methods can be in the kit. Preferred and detailed descriptions of the inventive methods read alike on suitability and resulting cultures or aggregates of the inventions. All embodiments can be combined with each other, except where otherwise stated.

DETAILED DESCRIPTION

As shown in FIG. 1a, the present invention relates to a method of improved organoid formation. The method can be divided in at least two part-methods, which independently already provide beneficial results. I.e. the first steps result in an elongated or fiber-supported aggregation of cells that already has beneficial developmental potential in any later culturing method. This elongated or fiber-supported aggregation of cells is by some definitions an embryoid body and also forms an aspect of the invention. The second series of steps as illustrated in FIG. 1a further develop the aggregation of cells into an artificial tissue culture with improved characteristics. This method and the resulting artificial tissue culture, also termed organoid, form a further—but related—aspect of the invention.

The initial method of generating an elongated or fiber-supported multicellular aggregation of multipotent cells comprises the steps of
a) providing a plurality of pluripotent or non-human totipotent cells that are located in an oblong or longish arrangement,
b) letting said cells grow and differentiate in said arrangement, wherein said cells form intercellular attachments (such as bonds or junctions) and adhere to each other.

The inventive method usually starts with providing a plurality of pluripotent cells. The cells may also be differentiated or undifferentiated. The cells may also be totipotent, if ethical reasons allow. In certain embodiments, especially if totipotent, the cells are preferably non-human cells. In other embodiments, the cells may be human cells.

A "totipotent" cell can differentiate into any cell type in the body, including the germ line following exposure to stimuli like that normally occurring in development. Accordingly, a totipotent cell may be defined as a cell being capable of growing, i.e. developing, into an entire organism. The cells used in step a) are preferably not totipotent, but (strictly) pluripotent.

A "pluripotent" stem cell is not able of growing into an entire organism, but is capable of giving rise to cell types originating from all three germ layers, i.e., mesoderm, endoderm, and ectoderm, and may be capable of giving rise to all cell types of an organism. Pluripotency can be a feature of the cell per see, e.g. in certain stem cells, or it can be induced artificially. E.g. in a preferred embodiment of the invention, the pluripotent stem cell is derived from a somatic, multipotent, unipotent or progenitor cell, wherein pluripotency is induced. Such a cell is referred to as induced pluripotent stem cell herein. The somatic, multipotent, unipotent or progenitor cell can e.g. be used from a patient, which is turned into a pluripotent cell, that is subject to the inventive methods. Such a cell or the resulting tissue culture can be studied for abnormalities, e.g. during tissue culture development according to the inventive methods. A patient may e.g. suffer from a birth defect or congenital disorder. Characteristics of said defect or disorder can be reproduced or studied with the inventive aggregates and tissue cultures.

Preferred starting cells are stem cells, such as embryonic stem cells as described in WO 03/046141 or Chung et al. (Cell Stem Cell 2, 2008, 113-117), which are not derived from an (human) embryo stricto sensu, can be used. Such cells may be parthenotes or cultured cells. Most preferred cells are induced pluripotent cells.

A "multipotent" cell is capable of giving rise to at least one cell type from each of two or more different organs or tissues of an organism, wherein the said cell types may originate from the same or from different germ layers, but is not capable of giving rise to all cell types of an organism.

In contrast, a "unipotent" cell is capable of differentiating to cells of only one cell lineage.

A "progenitor cell" is a cell that, like a stem cell, has the ability to differentiate into a specific type of cell, with limited options to differentiate, with usually only one target cell. A progenitor cell is usually a unipotent cell, it may also be a multipotent cell.

With decreasing differentiation capabilities, stem cells differentiate in the following order: totipotent, pluripotent, multipotent, unipotent. During development of the inventive organoid, stem cells differentiate from pluripotent (also totipotent cells are possible) into multipotent stem cells, further into unipotent stem cells and subsequently into non-stem tissue cells. In case of neuronal tissue, tissue cells may e.g. be neuronal cells or neuroepithelial cells, such as glial cells.

The cells of step a) are arranged or located in an oblong or longish arrangement. Oblong or longish arrangements may be in a row with one or more cells in thickness, whereas the oblong dimension is larger than the width. The oblong or longish arrangement can be straight or in a curved line, wherein the length along the curve marks the length of the arrangement. The cells need not be in contact with each other, however, the distance should be small enough so that growing and multiplying cells during the method can come in contact with each other. Such distances between cells are e.g. 1 µm to 500 µm, preferably 5 µm to 300 µm or 15 µm to 200 µm or 20 µm to 100 µm, or at most 500 µm, at most 200 µm or at most 100 µm. The distance is preferably by the cells which are most apart.

Usually only a few cells are placed in the oblong or longish arrangement, preferably 2 to 500000 cells are located on the oblong or longish arrangement in step a). In preferred embodiments, the cell located or placed cell number is 4 to 400000, preferably 4 to 250000 cells, 8 to 100000 cells, 12 to 75000 cells, 20 to 50000 cells, 30 to 25000 cells, 40 to 10000 cells, or 50 to 8000 cell. Such a cell amount shall facilitate the development of the inventive multicellular aggregation in the oblong or longish geometry and preferably further the inventive in vitro grown tissue culture after further differentiation of the multicellular aggregation, in particular each with the sizes and dimensions disclosed herein.

The oblong or longish arrangement can be facilitated by any means. A practical means is by adherence to a support, which will be explained in more detail below. Other possibilities exist, like a placement in suspension. However, it is preferred that due to polarity of most cells the orientation of the cells during growth can develop uniformly, wherein the same polar side, such as a ventricular side or a basolateral side of cells shows into the same direction with regard to the centre or with regard to an axis of the developing multicellular arrangement. Of course bulges and bents are possible, so axis or centre should not be understood in a strict mathematical fashion but as a parameter of local cell behaviour. In other terms, the cells may have or develop a surface, which has the same polarity/cell orientation. Such a cell surface may be in contact with a support or be directed away from a support.

Preferably the cells are not arranged in a cavity, e.g. of a porous support. Inside a cavity, the cells would not be able to develop with a uniform polarity since various, multiple surface contacts would be form, each with their own polarity resulting in an essentially random orientation in the final multicellular arrangement or tissue culture.

The oblong or longish arrangement preferably has an aspect ratio of a prolate dimension (length) to a perpendicular dimension (width) of at least 2:1, preferably of at least 3:1, of at least 4:1, of at least 5:1, of at least 6:1, of at least 7:1, of at least 8:1, of at least 9:1, or of at least 10:1. The width can be any perpendicular dimension to the prolate dimension;

preferably it is the broadest width. The width is usually determined in the center of the prolate dimension but again the perpendicular dimension can be along the entire length (following curves or bents, if present as mentioned above) of the prolate dimension.

In step b), the cells are grown and allowed to differentiate. Differentiation into a tissue type of choice can be facilitated by use of growth or differentiation factors, which will be explained below in more detail below with regard to target cell types. The multicellular arrangement of cells is not necessarily fully developed into a given tissue type but usually has taken the first steps during differentiation, e.g. from pluripotent cells or cells with similar broad developmental capacity, towards multipotent cells, e.g. cells with reduced developmental capacity. Such a development direction can be towards neuronal or neurogenic, adipogenic, myogenic, tenogenic, chondrogenic, osteogenic, ligamentogenic, dermatogenic, hepatic, or endothelial differentiation. Preferred differentiation is into neuronal cells. Accordingly, the invention relates to a method of differentiating microfilament-borne cell aggregates, in particular, embryoid bodies, towards neural lineage and thereby generation of micropatterned (due to the arrangement in step a) three dimensional neural tissue. Preferably, step, b) is in suspension culture.

The important aspect of step b) is the formation of the aggregate, which will be similar oblong or longish due to the arrangement or localization during step a). To form an aggregate, the cells connect to each other and form intercellular bonds. The aggregation of the cells can also be called a multicellular body. If totipotent or pluripotent stem cells are used in step a) then it may also be called embryonic body due to the initial broad developmental and differentiation capacity. In step b) the cells are grown and they multiply. Suitable media as known in the art and exemplified in the examples and in the kit description below can be used. Cell multiplication in this step can e.g. by a factor of 10, of 100, of 1000 or of 3000 or any range in between these values. Usually the aggregate remains rather small at this stage, e.g. measuring up to 5 mm or at most 10 mm in the oblong dimension. Essentially the same values for aspect ratios as disclosed above for the arrangement can be seen in the elongated or fiber-supported multicellular aggregation. The aspect ratio itself may of course vary between steps a) and b) due to cell growth, especially in the width/perpendicular dimension.

In preferred embodiments, in step a) said plurality of cells is adhered to a support. According to this embodiment, the support is used to arrange the cells in the oblong or longish arrangement. Accordingly, the support acts as a scaffold for the cells or multicellular aggregate that is forming due to cell growth. After the cells have grown and adhered to each other, the support is no longer needed. The support helps to by patterning the growth of the cells in three dimensions. It can be dissolved or bio-resorbed after step b). Such a support, especially as will be explained in detail below can be provided in the inventive kit.

Accordingly the invention provides a method of culturing and expanding undifferentiated or differentiated cells from pluripotent stem cells (such as embryonic stem cells or induced pluripotent stem cells) on a support, e.g. a non-porous biocompatible scaffold.

Preferably the support is a non-porous microfilament scaffold. Preferably 1 to 50, e.g. 2 to 40, 3 to 30, 5 to 20 or 6 to 12 such microfilament supports are used.

Preferably the support has a rod-shaped or grid-shaped or fibrous structure. The support may be microfilaments. Preferably, the support has an aspect ratio of the length:width (broadest width) of at least 2:1, preferably of at least 3:1, of at least 4:1, of at least 5:1, of at least 6:1, of at least 7:1, of at least 8:1, of at least 9:1, of at least 10:1 or of at least 15:1. The structures may be dimensioned as described above, especially with regard to the cell arrangements above, such as the structures may be straight or bent. The support may have a length of 20 µm to 20 mm and/or a diameter of 1 µm to 60 µm. Preferably the length is about 50 µm to 10 mm, e.g. 200 µm to 5 mm or 500 µm to 3 mm. The width or diameter may be 2 µm to 50 µm, preferably 10 µm to 40 µm or 20 µm to 30 µm. Preferably the support has or least two ends (in non-branched, or more than two ends (if branched, e.g. 3, 4, 5, 6, 7, 8 or more ends). The length is determined according to the longest end to end distance following the curves and bends of the support structures. The structure may have circular or no circular elements. If circular elements are present, then they shall be long enough as not to disturb uniform polarity of the aggregate as described above. Other non-disturbing circular elements may be only a small fraction of the overall support and hence uniform polarity may form undisturbed on the majority of the non-circular part of the support. As to the also possible the grid-shape, the support may be composed of crossed or interlacing rods or fibres according to the rod-shaped or fibrous structures defined above. The lattice must be large enough so as not to form uniform polarity disturbing cell aggregates. The same as said for circular shapes also applies to grid-shapes. It is important that an oblong culture results with a larger surface to volume ratio than found in a globular cell structure is obtained. Elongated structure increases immediate surface and helps later in the development of convoluted structures, which even further increase the surface to volume ration beyond that of a rod shaped cell aggregation. The elongated shape may or may not be circular. In order to achieve the increased surface to volume ratio, the culture needs only to be partially elongated, especially according to the above dimensions, it may extend further and be even circular or grid shaped. Circle or grid diameter may e.g. be at least 50 µm or at least 100 µm. The rod-shaped or fibrous-shaped supports may interlace even without forming a grid, which is preferred according to the invention (see FIGS. 1c, d and e and 7).

The support can be of any material suitable to support cells, especially allowing an oriented adherence of polar cells. E.g. the apical or basolateral side of polar cells may adhere to the support.

Example support materials are polymers (e.g. organic polymers that are or are not biopolymers), macromolecules and inorganic materials. Such materials are preferable on the surface of the support, especially the cell contacting surface. The material of the support or the supports surface is preferably a macromolecule selected from poly(ethylene glycol), including its derivatives with one or more H or a monomer unit substitutes by an organic residue, such as $C_1$-$C_8$ residues, optionally with O, N, P or S replacing a C, preferably $C_1$-$C_5$ residues; Further support materials selected from polyisobutylene, polyoxazolines, poly(Nisopropylacrylamide), polyisobutylene, caprolactone, polyimide, polythiophene, polypropylene/polyethylene, polyacrylic, polyvinylpyrrolidone, polyvinylalcohol. A macromolecule is a very large molecule commonly, but not necessarily, created by polymerization of smaller subunits. The subunits of the macromolecule or polymer may be homogenous or heterogeneous. Typically, "hydrocarbon chains" include linear, branched or dendritic structures. A polymeric backbone chain is the chain of molecules that without side-residues link the macromolecule from beginning to end. Different forms of hydrocarbon chains may differ in molecular weights, structures or geometries (e.g. branched, linear, forked hydrocarbon chains, multifunctional, and the like). Hydrocarbon chains for use in the present invention may preferably comprise one of the two following structures: substituted or unsubstituted —$(CH_2)_m$— or —$(CH_2)_n$-Het-$(CH_2)_o$—, dendrimers of generations 1 to 10 where m is 3 to 5000, n and o are independently from another 1 to 5000 and Het is a heteroatom, wherein the terminal groups and architecture of the overall hydrocarbon chains may vary. E.g. in the final particle there will be an anchor group which is formed by the linker molecule. This description includes any linear or branched hydrocarbon chains with ratios of unsaturated: saturated bonds varying from 0:100 to 100:0. In some embodiments the hydrophobic spacer comprises e.g. >50% of subunits that are —$CH_2$—. Preferably the polymer backbone chain comprises O. In alternative or combined embodiments at least 10% of the carbon atoms, e.g. 10% to 50%, more preferred 20% to 40%, of the hydrocarbon chains are substituted by a heteroatom. Heteroatoms may be selected from O, N, S or N, preferably O. Side chain substitutions can be at a C or at Het with the substituents being selected independently from heterosubstituted or non-heterosubstituted, branched or unbranched, saturated or unsaturated hydrocarbons with 1 to 20 atoms, preferably 2 to 10, especially preferred 2 to 6 atoms in length. Any of these substances may be substituted by as $C_1$-$C_8$ residues, optionally with O, N, P or S replacing a C, preferably $C_1$-$C_5$ residues. Further possible substituents are halogens, like Cl, F. Also possible is PVC.

The molecules of the support material may have an average mass of 10 kDa to 30000 kDa, preferably of 50 kDa to 20000 kDa, especially preferred of 100 kDa to 15000 kDa or 1000 kDa to 10000 kDa.

Preferably the support of rod-shaped or lattice-shaped or fibrous structure is of a polymeric material, preferably comprises or consists of a polyethylenglycol backbone chain. Such a backbone chain is —O—$CH_2$—$CH_2$—. Any side chain substituents instead of H as described above are possible, preferably $CH_3$, $C_2CH_3$, OH, $NH_2$, =O, alone or in combination; e.g. $CH_3$ as first substituent and any other as a second substituent, in particular O, such as found in polylactic acid. Preferred polymers are polylactic acid and/or polyglycolide, especially a mixture or copolymer of these polymers.

As used herein, "comprising" shall be understood as referring to an open definition, allowing further members of similar or other features. "Consisting of" shall be understood as a closed definition relating to a limited range of features. Any embodiment that comprises one or more specified element(s), may—if not explicitly stated to the contrary—also consist of this/these element(s).

Possible biopolymers are e.g. polyglycosides, macromolecular carbohydrates, such as cellulosic materials, or solid protein complexes, especially denatured or inactive proteins. The usability of cellulosic materials may depend on the cell type used and for most cells it is not preferred. E.g. US 2011/143433 A2, FIG. 168, and comparative examples herein show that cellulose for some cells leads to bulbous instead of oblong or longish arrangements that are needed according to the invention. Therefore pure cellulose is preferably not a material for the fibrous support. According to the invention the oblong or longish arrangements form by deposition of the cells on the fiber support and filling of remaining gaps by cell growth so that entire support fibers are covered by the cells. An oblong or longish arrangement may be maintained by the cells throughout embryoid body formation, wherein the cells differentiate and grow further. In addition to biocompatible synthetic polymers that are not a biopolymers, proteins are also highly preferred. Proteins can be used as fibrous support for the inventive differentiation method. Such proteins fibrous support may be collagen-comprising microfibers such as gelatin ribbons or fibers that can be produced by wet-spinning (e.g. as described in Han et al., Adv. Funct. Mater. 2012, DOI: 10.1002/adfm.201201212, adapted to the dimensions of the fibers as disclosed herein; cross-linking as described by Han to create a sponge is not needed).

Preferably the support is a polymer microfilament.

Preferably the support is non-porous or has a low porosity of less than 5% (v/v) of the support's volume. As said above, it is advantageous to prevent cavities in which essentially nonoriented aggregates of polar cells assemble. Preferably the porosity is less than 4%, less than 3%, less than 2%, less than 1% or 0% (all % values v/v).

The support may be biocompatible, preferably it is not bioactive, i.e. it does not interact with the cells besides the attachment and the orientation determination, which is usually due to the attachment. It is preferably not metabolized by the cells. In other embodiments it may be (slowly) deconstructed or depolymerized by the medium or by the cells. E.g. it may be hydrolysable. Since the support is only needed for the arrangement, it may be removed without disturbing the cell, i.e. breaking the oblong multicellular arrangement after said arrangement has formed by intercellular bonding connections.

The cells can be stimulated to differentiate by contacting the cells with a tissue specific growth or differentiation factor. Such a tissue specific growth or differentiation factor may be a neuronal or neurogenic, myogenic, tenogenic, chondrogenic, or osteogenic differentiation factor, especially preferred a neuronal differentiation factor. This will determine the development into the respective type of cellular tissue in later development. The cells will thereby transit from pluripotent to multipotent cells. Other tissue types shall then be not or only by a return to a pluripotent status be possible again. Usually not all cells are differentiated to the selected tissue type. It usually sufficient when about 30% or more or at least 40% or at least 50%, or at least 60% or at least 70% or at least 80% of the cells initiate differentiation towards the selected tissue type and transform to reduce their differentiation potential by multipotent cell with the respective tissue destiny. Of course this differentiation destiny only applies for the cells that are not returned to a un- or less differentiated state by use of artificial growth and dedifferntiation stimuli. Clearly, even somatic cells can be returned to a pluripotent cells and this is not meant when defining a differentiated state herein. Preferably, not factors are introduced to the cells that would return the cells to pluripotent cells.

The present invention also relates to an elongated or fiber-supported multicellular aggregation of multipotent cells obtainable by the inventive method, especially obtained after step b).

An elongated or fiber-supported multicellular aggregation of multipotent cells of the invention may comprise multipotent cells that are arranged in an oblong or longish arrangement with an aspect ratio of a prolate dimension to a perpendicular dimension of at least 2:1, preferably of at least 5:1 (or any of the above disclosed for the arrangement in step a). The aggregation may comprise cells at different stages of differentiation. This may relate to pluripotent and different differentiated multipotent cells that may be directed towards different lineages of the tissue differentiation of choice (e.g. neuronal or neurogenic, myogenic, tenogenic, chondrogenic, or osteogenic). In most preferred embodiments said aggregate contains polar cells and said polar cells with a uniform orientation with respect to the center of said aggregate (as described above bulges and the like are possible). Preferably said polar cells constitute at least 50%, or at least 60% or at least 70%, of the cells of the aggregation.

The support as described above may still be in the aggregation. Preferably the aggregation comprises a central support, around which the cells have grown. This is achieved by letting the cells grow according to the inventive method.

The aggregation is grown in the inventive methods and it may have more cells than originally placed in step a). For example, the aggregation of cells may comprise between 8000 and 100 million cells, preferred cell ranges are e.g. 10000 to 50 million, 100000 to 20 million, 500000 or 10 million, but also 8000 or more, 10000 or more, 100000 or more, 500000 or more. Preferably the cell aggregates remain small in size for later culturing, especially as described below, such as by step p) or further step q). Related thereto, the cell aggregation may have a size (length, longest dimension, optionally following the curvature) of between 50 μm to 40 mm, preferably between 70 μm to 10 mm, 100 μm to 5 mm or between 150 μm to 1mm.

The cells of the aggregation may have initiated differentiation towards a particular differentiation fate. They may have become multipotent (from previously pluripotent or even less differentiated), some cells may even be unipotent or somatic tissue cells. The tissue fate may be towards any tissue. Preferably, the target tissue is selected from neuronal tissue, connective tissue, hepatic tissue, pancreatic tissue, kidney tissue, bone marrow tissue, cardiac tissue, retinal tissue, intestinal tissue, lung tissue, and endothelium tissue. For example the aggregation of cells may comprise any cell stem cell for such a tissue that has undergone tissue specific differentiation. Preferably the aggregation comprises cells selected from neuronal or neurogenic, adipogenic, myogenic, tenogenic, chondrogenic, osteogenic, ligamentogenic, dermatogenic, hepatic, or endothelial cells. In some cases, also combinations are possible, e.g. organ cells (e.g. neuronal, myogenic, hepatic) with cells that would develop into supporting tissues (e.g. endothelial, adipogenic, ligamentogenic cells). In the methods, differentiation may be initiated by commonly known tissue specific growth or differentiation factors, also called, differentiationinducing agents. Such are e.g. known in the art and are e.g. disclosed in WO 2009/023246 A2, WO 2004/084950 A2 and WO 2003/042405 A2. Further, the differentiating or growth factor can be a bone morphogenetic protein, a cartilage-derived morphogenic protein, a growth differentiation factor, an angiogenic factor, a platelet-derived growth factor, a vascular endothelial growth factor, an epidermal growth factor, a fibroblast growth factor, a hepatocyte growth factor, an insulin-like growth factor, a nerve growth factor, a colony-stimulating factor, a neurotrophin, a growth hormone, an interleukin, a connective tissue growth factor, a parathyroid hormone-related protein, (e.g. disclosed in WO 2004/084950 A2). These factors/agents are commercially available and need no further description. Of course, such factors/gents may for any one of the above tissue types may be included in the inventive kit. Preferably, neuronal or neurogenic are used in the method or provided in the kit and preferably neuronal or neurogenic cells are present in the inventive aggregation.

The aggregation may comprise progenitor cells, such as a stem cell, to any tissue, especially those described above. The progenitor cell is preferably selected from the group consisting of a totipotent stem cell, pluripotent stem cell, multipotent stem cell, mesenchymal stem cell, neuronal stem cell, hematopoietic stem cell, pancreatic stem cell, cardiac stem cell, embryonic stem cell, embryonic germ cell, neural stem cell, especially a neural crest stem cell, kidney stem cell, hepatic stem cell, lung stem cell, hemangioblast cell, and endothelial progenitor cell. The pluripotent cell used in the method or the progenitor cell can be derived from a de-differentiated chondrogenic cell, myogenic cell, osteogenic cell, tendogenic cell, ligamentogenic cell, adipogenic cell, or dermatogenic cell.

The inventive aggregation of cells can be cultured further, in particular towards and into an artificial tissue. Accordingly, the invention also provides a method of generating an artificial tissue culture comprising, o) providing an elongated or fiber-supported multicellular aggregation of multipotent cells, preferably as defined above, p) culturing said elongated or fiber-supported multicellular aggregation in a three dimensional matrix, preferably a gel, wherein said cells are allowed to differentiate, thereby expanding said cells, and q) culturing said expanded cells of step p) in a suspension culture.

These method steps resemble the steps as described in WO 2014/090993 A1, which is fully incorporated herein by reference. Especially the examples of WO 2014/090993 A1 can be employed according to the present invention (see also FIG. 1a of the reference for an overview). In brief, culturing in a three dimensional matrix, preferably a gel, increase the developmental potential of the cells and allows improved tissues. Using the inventive elongated or fiber-supported aggregation of cells further improves the developmental capacity, growth and consistency beyond the artificial tissues described in WO 2014/090993 A1. The use of the oblong or longish aggregation leads to more convoluted structures with additional cellular development. E.g. the inventive tissue cultures can develop a radially organized cortical plate.

The method can be even further improved by additional step r) of adding dissolved material of a three dimensional matrix (the same or different than in step p)) to said suspension culture, whereby the dissolved material adheres to the culture and forms a matrix. The dissolved material of a three dimensional matrix is dissolved extracellular matrix. The addition of the matrix material can lead to a further stabilization of the growing tissue culture, which can grow out of the initial three dimensional matrix provided in step p) (such as a droplet of the matrix). The additional matrix material of step r) may attach and establish further matrix, either as stabilizing cell coating, at least in parts, or as a gel. This allows a more stabilized growth allowing bigger cultures that may even develop further due to the reduction of size restrictions.

Related thereto, the invention also provides a method of generating an artificial tissue culture comprising, u) providing multicellular aggregation of multipotent cells, preferably as defined above, v) culturing said multicellular aggregation in a three dimensional matrix, preferably a gel, wherein said cells are allowed to differentiate, thereby expanding said cells, w) culturing said expanded cells of step v) in a suspension culture, and r) adding dissolved material of a three dimensional matrix to said suspension culture, whereby the dissolved material adheres to the culture and forms a matrix, preferably wherein the dissolved material of a three dimensional matrix is dissolved extracellular matrix.

The method of steps v) to w) and r) is essentially the same as method o) to q) and r) with the use of a different cell aggregation. Here, the cells do not require the oblong or longish structure. Cells obtainable without placement/location in step a) may be used. Such aggregates may be similar to known embryoid bodies known in the art, or differentiation initiated neuroectoderm, when neural induction medium is used (e.g. as in WO 2014/090993 A1). As said above, step r) can improve any culture and allow further growth. The same as said above for the oblong or longish culture, e.g. size, or differentiation type, also applies to the aggregation provided in step o), with the only exception being the shape, which may be spherical.

Preferably, the cells only initiated differentiation before step o)/u), e.g. during culturing of the aggregation of cells. In the later steps, especially during step p)/v) in the three dimensional matrix no tissue specific differentiation factor or agent is added. It is possible to use standard differentiation medium instead of tissue specific medium. This does not mean that no differentiation takes place, on the contrary, endogenous growth factors may be produced by the cells and a differentiation, especially towards the destiny selected previously, is happening.

The three dimensional matrix may be a gel, especially a rigid stable gel, which results in further expansion of growing cell culture/tissue and differentiation. A suitable three dimensional matrix may comprise collagen. More preferably the three dimensional matrix comprises extracellular matrix (ECM) or any component thereof selected from collagen, laminin, entactin, and heparin-sulfated proteoglycan or any combination thereof. Extracellular matrix may be from the Engelbreth-Holm-Swarm tumor or any component thereof such as laminin, collagen, preferably type 4 collagen, entactin, and optionally further heparan-sulfated proteoglycan or any combination thereof. Such a matrix is Matrigel. Matrigel is known in the art (U.S. Pat. No. 4,829,000) and has been used to model 3D heart tissue previously (WO 01/55297 A2). Preferably the matrix comprises a concentration of at least 3.7 mg/ml containing in parts by weight about 60-85% laminin, 5-30% collagen IV, optionally 1-10% nidogen, optionally 1-10% heparan sulfate proteoglycan and 1-10% entactin. Matrigel's solid components usually comprise approximately 60% laminin, 30% collagen IV, and 8% entactin. Entactin is a bridging molecule that interacts with laminin and collagen. Such matrix components can be added in step r). These components are also preferred parts of the inventive kit. The three dimensional matrix may further comprise growth factors, such as any one of EGF (epidermal growth factor), FGF (fibroblast growth factor), NGF, PDGF, IGF (insulin-like growth factor), especially IGF-1, TGF-β, tissue plasminogen activator. The three dimensional matrix may also be free of any of these growth factors.

In general, the three dimensional matrix is a three dimensional structure of a biocompatible matrix. It preferably comprises collagen, gelatin, chitosan, hyaluronan, methylcellulose, laminin and/or alginate. The matrix may be a gel, in particular a hydrogel. Organo-chemical hydrogels may comprise polyvinyl alcohol, sodium polyacrylate, acrylate polymers and copolymers with an abundance of hydrophilic groups. Hydrogels comprise a network of polymer chains that are hydrophilic, sometimes found as a colloidal gel in which water is the dispersion medium. Hydrogels are highly absorbent (they can contain over 99% water) natural or synthetic polymers. Hydrogels also possess a degree of flexibility very similar to natural tissue, due to their significant water content. It is possible that the three dimensional matrix, or its components, especially ECM or collagen, still remains in the produced tissue culture.

Although any tissue can be grown by the inventive methods, especially those mentioned above with regard to the aggregation of cells, during the production of which usually the differentiation fate is selected; the invention preferably is used to produce neuronal tissue. In particular, the invention can be used to produce an artificial densely packed array of neurons in a radial organisation resembling the initial condensed postmitotic neuronal lamina of the developing brain. Also this method can be improved by the additional step r), especially by further comprising the step of adding dissolved extracellular matrix components.

During culturing of the cells towards the artificial tissue the cells are expanded and may differentiate into unipotent stem cells and/or even into somatic tissue cells. Various cells at different stages of differentiation are possible and even some pluripotent cells may remain. Preferably, there are between 0.1% and 40%, preferably between 1% and 20%, pluripotent cells in the tissue culture.

The invention also provides an artificial tissue culture obtamable by a method of the invention. The culture may be of any tissue mentioned above. "Artificial" means that it is grown in vitro and has certain characteristics of artificial cultures, like size, consistency, shape and cell organization. The shape may be irregular and different from natural occurring tissues and cell organization may differ due to size restrains. In particular, "artificial" excludes naturally occurring tissues and organs and their parts, e.g. tissue slices. The three dimensional matrix may be still in the culture and/or the artificial tissue may have the shape determined by growth in such a matrix. E.g. the culture may be obtainable by growth in a three dimensional matrix, especially those as described above. Preferably, the inventive tissue is an organoid, especially a cerebral organoid (en.wikipedia.org/wiki/Cerebral organoid).

As said, a preferred tissue is neuronal tissue. Provided is an inventive artificial neuronal tissue culture comprising a cortical plate; preferably wherein said tissue culture is in vitro grown from an aggregate of cells and/or is not a culture of an in vivo developed brain or a tissue sample thereof. The radially organized cortical plate is a hallmark of highly evolved brain tissue, such as human brain, and shows a high level of development that is achievable with the present invention. The cortical plate is herein also referred to as radially organized cortical plate to emphasize its radial organization that is also found in natural brains.

The radially organized cortical plate may comprising the expression markers Ctip2, Map2, DCX, or any combination thereof, especially Ctip2, Map2 and DCX, preferably further comprising Map2. Such markers can be detected by binding to a ligand, e.g. an antibody. Such binding events can be visualized by a label, e.g. an optical label such as a fluorescent label. The label may be bound to the ligand.

The artificial tissue culture may also comprise radial glia, preferably linear units of radial glia and neurons. Radial glia, especially outer radial glia has been observed before (WO 2014/090993 A1) and may also be found in the inventive culture.

The inventive neuronal culture may also comprise a basement membrane. The basement membrane usually comprises laminin, in fact it may be rich in laminin.

Preferably the basement membrane covers a basal surface of neuroepithelium.

Preferably the basement membrane is outside of migrating neurons.

In a further preferment the culture contains neurons and/or radial glia radially organized relative to one another in a manner reminiscent of radial units seen in vivo. Preferably, the radial glia is based on a basal process that extends the width of the tissue into the cortical plate.

Preferably, the culture comprises a dorsal cortex and/or comprises dorsal cortical markers Tbr2 and/or Tbr1.

All of these preferred embodiments are of course combinable.

The inventive cell aggregation and/or the tissue cultures can be used as model for organ or tissue behaviour or development. Substances or environmental changes can be tested on any effects on organ or tissue functions and/or development during growth and differentiation. Likewise, similar to substances genetic modifications, especially mutations that alter gene function, can be tested on these effects. Multiple substances or environmental changes or genetic modifications can be tested, especially to test for an added or reduced effect in comparison to a first substance/environmental change/genetic modification. Accordingly, especially in disease causing substance/environmental change/genetic modification causative or curative substances/environmental changes/genetic modifications can be investigated or identified (screening). Such effects are usually studied in comparison to a control. The control may not be treated by the (or the additional) substance/environmental change/genetic modification under investigation.

In particular preferred, the inventive methods or cultures can be used to test for side effects in drug candidates. Preferably, causes, the nature and possible cures for congenital disorders are investigated by monitoring for any changes. For example, teratogenic effects can be tested by monitoring the development and/or growth of the inventive cell aggregate and/or tissue culture when contacted by a potentially causative substance/environmental change/genetic modification.

Accordingly, the invention provides the use of the inventive cell culturing methods and cell aggregates and tissues in methods of investigating genes and drugs for tissue culture altering effects. Genes may be up- or downregulated for this purpose. Drugs can be added to the culture during any stage, preferably stages b) and/or p) to q) or v) to w) and/or r). By this method, developmental disorders influenced by (defective) genes or by harmful (e.g. teratogenic) drugs or compounds or other environmental influences can be investigated. If an effect is only expected during initial differentiation, contacting during step b) may be sufficient. If an effect is expected during later differentiation and/or cell arrangement or growth after differentiation (e.g. an organ specific teratogen), contacting during step p) and/or q) optionally with r)—or during v) and/or w) optionally with r) may be sufficient. Of course, this can be combined with contacting during step b). Such a teratogenic compound is for example ethanol, which leads to fetal alcohol disorders such as fetal alcohol syndrome if an embryo or fetus is exposed to it during development. The effects of ethanol on developing tissues, e.g. brain tissues during development can be investigated with the inventive method.

According to one preferment, the invention provides the method of investigating a developmental tissue effect comprising i) decreasing or increasing the expression in a gene of interest in a cell or ii) administering a candidate drug to the cells, at any stage during the inventive method (as above, e.g. steps b), o) to q) and/or u) to w)).

Also provided is a method of screening a candidate therapeutic agent suitable for treating a developmental tissue defect of interest, comprising performing the inventive culturing method and administering the candidate agent to said cells at any stage during the method (as above), preferably at all stages.

Also provided is a method of testing a candidate drug for developmental effects, especially for congenital disorder effects, comprising administering a candidate drug to an artificial culture according to the invention or during the methods (e.g. stages as above) and determining an activity of interest of the cells of said culture and comparing said activity to an activity of cells to the culture without administering said candidate drug, wherein a differential activity (to a control) indicates a developmental effect.

Further provided is a kit of compounds and substances. The kit may comprise means to perform any of the inventive methods. Of course not all substances need to be included since some are standard chemicals or usually available. Nevertheless, preferably the core elements are provided. In other kits, rarer elements are provided. Of course the inventive kits or their substances may be combined. Components in the kit are usually provided in separate containers, such as vials or flasks.

A kit is provided, comprising i) a solid support of rod-shaped or lattice-shaped or fibrous structure, which is preferably solid and/or non-porous and/or defined as described above, and comprising ii) a three-dimensional matrix, preferably a gel and/or a extracellular matrix or any component thereof selected from collagen, laminin, entactin, and heparin-sulfated proteoglycan or any combination thereof, in particular preferred an extracellular matrix from the Engelbreth-Holm-Swarm tumor, especially preferred matrigel. Solid supports i) are described in more detail above and any described embodiment, e.g. with regard to size, shape or material may be provided in the kit. Likewise, three-dimensional matrices are described above and any material may be provided in the kit.

Also provided is a kit further comprising vitamin C; vitamin A, 2-mercaptoethanol; bFGF; ROCK inhibitor; insulin; a GSK3beta inhibitor; a Wnt activator, preferably CHIR 99021; an antibacterial agent, preferably Penicillin and/or Streptomycin; a SMAD inhibitor, preferably dorsomorphin and/or SB-431542; a retinoid, preferably retinoic acid; or any combination thereof. A preferred combination is the solid support and/or a three-dimensional matrix, either or both with vitamin C. A preferred kit comprises one or more of these compound together with the rod-shaped or lattice-shaped or fibrous support.

Any kit may further comprise cell growth nutrients, preferably DMEM/F12, fetal bovine serum, minimum essential medium (MEM), non-essential amino acid (NEAA), neural induction medium, Glutamax, or any combination thereof.

Preferably the support of rod-shaped or lattice-shaped or fibrous structure is biodegradable—as mentioned above, e.g. hydrolysable. In a further preferment of a kit, the support of rod-shaped or lattice-shaped or fibrous structure is of a polymeric material, preferably comprises a polyethylenglycol chain, more preferred wherein the support comprises or consists of polylactide, polyglycolide or combinations thereof. Of course any other material as described above is also possible.

It is contemplated that any method or product described herein can be implemented with respect to any other method or product described herein and that different embodiments may be combined.

The claims originally filed are contemplated to cover claims that are multiply dependent on any filed claim or combination of filed claims.

The use of the word "a" or "an" when used in conjunction with the term "comprising" in the claims and/or the specification may mean "one", but it is also consistent with the meaning of "one or more", "at least one", and "one or more than one".

It is contemplated that any embodiment discussed herein can be implemented with respect to any method or product of the invention, and vice versa. Any embodiment discussed with respect to a particular condition can be applied or implemented with respect to a different condition. Furthermore, compositions and kits of the invention can be used to achieve methods of the invention.

Throughout this application, the term "about" may be used to indicate that a value includes the standard deviation of error for the device or method being employed to determine the value or in a set value may refer to ±10%.

Preferably, the present invention is defined as in the following embodiments:

1. A method of generating an elongated multicellular aggregation of multipotent cells comprising the steps of
   a) providing a plurality of pluripotent or non-human totipotent cells that are located in an oblong or longish arrangement,
   b) letting said cells grow and differentiate in said arrangement, wherein said cells form intercellular attachments and adhere to each other.
2. The method of embodiment 1, wherein said oblong or longish arrangement has an aspect ratio of a prolate dimension to a perpendicular dimension of at least 2:1.
3. The method of embodiment 1 or 2, wherein in step a) said plurality of cells is adhered to a support, optionally wherein said support is dissolved or bio-resorbed after step b).
4. The method of embodiment 3, wherein said support has a rod-shaped or grid-shaped or fibrous structure, preferably with an aspect ratio of at least as defined in embodiment 2.
5. A method of generating a fiber-supported multicellular aggregation of multipotent cells comprising the steps of
   a) providing a plurality of pluripotent or non-human totipotent cells that are arranged on a fibrous support,
   b) letting said cells grow and differentiate in said arrangement, wherein said cells form intercellular attachments and adhere to each other.
6. The method of any one of embodiments 3 to 5, wherein said support is non-porous or has a porosity of less than 5% (v/v) of the supports volume.
7. The method of any one of embodiments 3 to 6, wherein said support is a polymer microfilament and/or is biocompatible but not bioactive.
8. The method of any one of embodiments 3 to 7, wherein said support comprises a polyethylenglycol chain, preferably wherein the support comprises or consists of polylactide, polyglycolide or a combination thereof, or a cellulosic material.

9. The method of any one of embodiments 3 to 8, wherein said support has a length of 20 μm to 20 mm and/or a diameter of 1 μm to 60 μm.
10. The method of any one of embodiments 1 to 9, wherein 2 to 500000 cells are located on the oblong or longish arrangement in step a) and/or wherein the most apart cells are at least 1 μm apart.
11. The method of any one of embodiment 1 to 10, wherein said cells are stimulated to differentiate by a contacting the cells with a tissue specific growth or differentiation factor, preferably a neuronal or neurogenic, myogenic, tenogenic, chondrogenic, or osteogenic differentiation factor, especially preferred a neuronal differentiation factor.
12. A multicellular aggregation of multipotent cells obtainable by a method of embodiments 1 to 11.
13. An elongated or fiber-supported multicellular aggregation of multipotent cells wherein multipotent cells are arranged in an oblong or longish arrangement with an aspect ratio of a prolate dimension to a perpendicular dimension of at least 2:1, preferably of at least 5:1, or on a fibrous support, and wherein said aggregate contains cells at different stages of differentiation, and said aggregate contains polar cells and said polar cells with a uniform orientation with respect to the center of said aggregate, preferably wherein said polar cells constitute at least 50% of the cells of the aggregate.
14. The aggregation of cells according to embodiment 12 or 13, comprising a central support, preferably as defined in any one of embodiments 3 to 9.
15. The aggregation of cells according to any one of embodiments 12 to 14, comprising between 8000 and 100 Million cells and/or having a size of between 50 μm to 40 mm.
16. The aggregation of cells according to any one of embodiments 12 to 15, wherein the aggregation of cells comprises multipotent neuronal or neurogenic, adipogenic, myogenic, tenogenic, chondrogenic, osteogenic, ligamentogenic, dermatogenic, hepatic, or endothelial cells.
17. The aggregation of cells according to any one of embodiments 12 to 16, wherein said aggregation is an embryoid body.
18. A method of generating an artificial tissue culture comprising,
o) providing an elongated or fiber-supported multicellular aggregation of multipotent cells, preferably as defined in any one of embodiments 12 to 17,
p) culturing said elongated or fiber-supported multicellular aggregation in a three dimensional matrix, preferably a gel, wherein said cells are allowed to differentiate, thereby expanding said cells, and
q) culturing said expanded cells of step p) in a suspension culture.
19. The method of embodiment 18, further comprising the step r) adding dissolved material of a three dimensional matrix to said suspension culture, whereby the dissolved material adheres to the culture and forms a matrix, preferably wherein the dissolved material of a three dimensional matrix is dissolved extracellular matrix.
20. A method of generating an artificial tissue culture comprising,
u) providing multicellular aggregation of multipotent cells, preferably as defined in any one of embodiments 12 to 17,
v) culturing said multicellular aggregation in a three dimensional matrix, preferably a gel, wherein said cells are allowed to differentiate, thereby expanding said cells,
w) culturing said expanded cells of step v) in a suspension culture, and
r) adding dissolved material of a three dimensional matrix to said suspension culture, whereby the dissolved material adheres to the culture and forms a matrix,
preferably wherein the dissolved material of a three dimensional matrix is dissolved extracellular matrix.
21. The method of any one of embodiments 18 to 20, wherein said expanded cells differentiate into unipotent stem cells.
22. The method of any one of embodiments 1 to 11 followed by a method of any one of embodiments 18 to 20.
23. The method of investigating a developmental tissue effect comprising i) decreasing or increasing the expression in a gene of interest in a cell or ii) administering a candidate drug, such as ethanol, to the cells, at any stage during the method of any one of embodiments 1 to 11 and 18 to 22.
24. The method of screening a candidate therapeutic agent suitable for treating a developmental tissue defect of interest, e.g. an ethanol induced fetal alcohol disorder, comprising performing the method of embodiment 23 and administering the candidate agent to said cells at any stage during the method, preferably at all stages.
25. An artificial tissue culture obtainable by a method of embodiments 18 to 24.
26. An artificial neuronal tissue culture comprising a radially organized cortical plate; preferably wherein said tissue culture is in vitro grown from an aggregate of cells and/or is not a culture of an in vivo developed brain or a tissue sample thereof.
27. The artificial tissue culture of embodiment 25 or 26 comprising a basement membrane comprising laminin.
28. The artificial tissue culture of any one of embodiments 25 to 27 comprising a basement membrane covering a basal surface of neuroepithelium.
29. The artificial tissue culture of any one of embodiments 25 to 28 comprising a basement membrane outside of migrating neurons.
30. The artificial tissue culture of any one of embodiments 25 to 29 comprising a radially organized cortical plate comprising the expression markers Ctip2, Map2, DCX, or any combination thereof, especially Ctip2, Map2 and DCX, preferably further comprising Map2.
31. The artificial tissue culture of any one of embodiments 25 to 30 comprising radial glia, preferably linear units of radial glia and neurons.
32. The method of testing a candidate drug, e.g. ethanol, for developmental effects, especially for congenital disorder effects, comprising administering a candidate drug to an artificial culture according to any one of embodiments 25 to 31 or during the methods of any one of embodiments 1 to 11 and 18 to 22 and determining an activity of interest of the cells of said culture and comparing said activity to an activity of cells to the culture without administering said candidate drug, wherein a differential activity indicates a developmental effect.
33. A kit comprising i) a solid support of rod-shaped or lattice-shaped or fibrous structure, which is preferably solid and/or non-porous and/or defined in any one of embodiments 6 to 9, and comprising ii) a three-dimensional matrix, preferably a gel and/or a extracellular matrix or any component thereof selected from collagen, laminin, entactin, and heparin-sulfated proteoglycan or any combination thereof, in particular preferred an extracellular matrix from the Engelbreth-Holm-Swarm tumor, especially preferred matrigel.

34. The kit of embodiment 33 further comprising vitamin C; vitamin A, 2-mercaptoethanol; bFGF; ROCK inhibitor; insulin; a GSK3beta inhibitor; a Wnt activator, preferably CHIR 99021; an antibacterial agent, preferably Penicillin and/or Streptomycin; a SMAD inhibitor, preferably dorsomorphin and/or SB-431542; a retinoid, preferably retinoic acid; or any combination thereof.

35. A kit comprising a rod-shaped or lattice-shaped or fibrous support, which is preferably solid and/or non-porous and/or defined in any one of embodiments 6 to 9, and at least a compound selected from vitamin C; vitamin A, 2-mercaptoethanol; bFGF; ROCK inhibitor; insulin; a GSK3beta inhibitor; a Wnt activator, preferably CHIR 99021; an antibacterial agent, preferably Penicillin and/or Streptomycin; a SMAD inhibitor, preferably dorsomorphin and/or SB-431542; a retinoid, preferably retinoic acid; or any combination thereof, preferably comprising a GSK3beta inhibitor and Wnt activator, preferably CHIR 99021.

36. The kit according to any one of embodiments 33 to 35 further comprising cell growth nutrients, preferably DMEM/F12, fetal bovine serum, minimum essential medium (MEM), non-essential amino acid (NEAA), neural induction medium, Glutamax, or any combination thereof.

37. The kit of any one of embodiments 33 to 36, wherein the support of rod-shaped or lattice-shaped or fibrous structure is biodegradeable.

38. The kit of any one of embodiments 33 to 37, wherein the support of rod-shaped or lattice-shaped or fibrous structure is of a polymeric material, preferably comprises a polyethylenglycol chain, more preferred wherein the support comprises or consists of polylactide, polyglycolide or combinations thereof.

The present invention is further illustrated by the following figures and examples, without being restricted to these embodiments of the invention.

BRIEF DESCRIPTION OF THE DRAWINGS

FIG. 8. a. RT-PCR for expression of markers of the three germ layers: Neuroectoderm (NE), mesoderm (ME), and endoderm (EN) in 20-day microfilament organoids and organoids lacking a filament (spherical organoids) both made from H9 cells. Neg. is the negative water control. b. Quantification of the mean ratio of individual lobes displaying positive staining for the specified regional markers (see FIG. 15$d$ for representative stained sections). Foxg1 positive regions represent forebrain, regions highly positive for Otx2 represent midbrain, En2 positive regions represent cerebellar or hindbrain identities. *$P<0.01$, **$P<0.0001$, Student's t-test, n=8 spheroids (40-day, H9) from three independent batches, n=11 enCOR organoids (40-day, H9) from four independent batches. c. Representative sections of whole 40-day H9 organoids stained for the forebrain marker Foxg1. enCORs display increased numbers of Foxg1+ lobes (arrows) compared with spheroids. d. Heatmap of Spearman correlation coefficients of differentially expressed genes at 60 days in H9 spheroids and enCORs with the Allen BrainSpan transcriptome20. All brain regions are shown for stage I (8-9 post-conception weeks, see FIG. 18$c$), sorted by anterior-posterior regional identity. Scale bars: 250 μm in FIG. 1$e$., 100 μm in FIG. 1$g$., 500 μm in FIG. 5$b$., FIG. 8$c$.

FIG. 18. Individual marker genes of pluripotency, germ layer identity and brain patterning a. Screen shots of the IGV view of single gene tracks of markers of pluripotency, neuroectoderm and mesendoderm in spheroid and enCORs at 20 days. b. Single gene tracks of markers of rostral-caudal and dorsalventral brain patterning in spheroid and enCORs at 60 days. Schematic of marker expression in the developing brain shown below. c. Heatmap of Spearman correlation coefficients between enCOR or spheroid 60 day samples and all brain regions at fetal timepoints from the Allen brainspan transcriptome, sorted by anterior-posterior regional identity and four stages of development.

Figure 21:
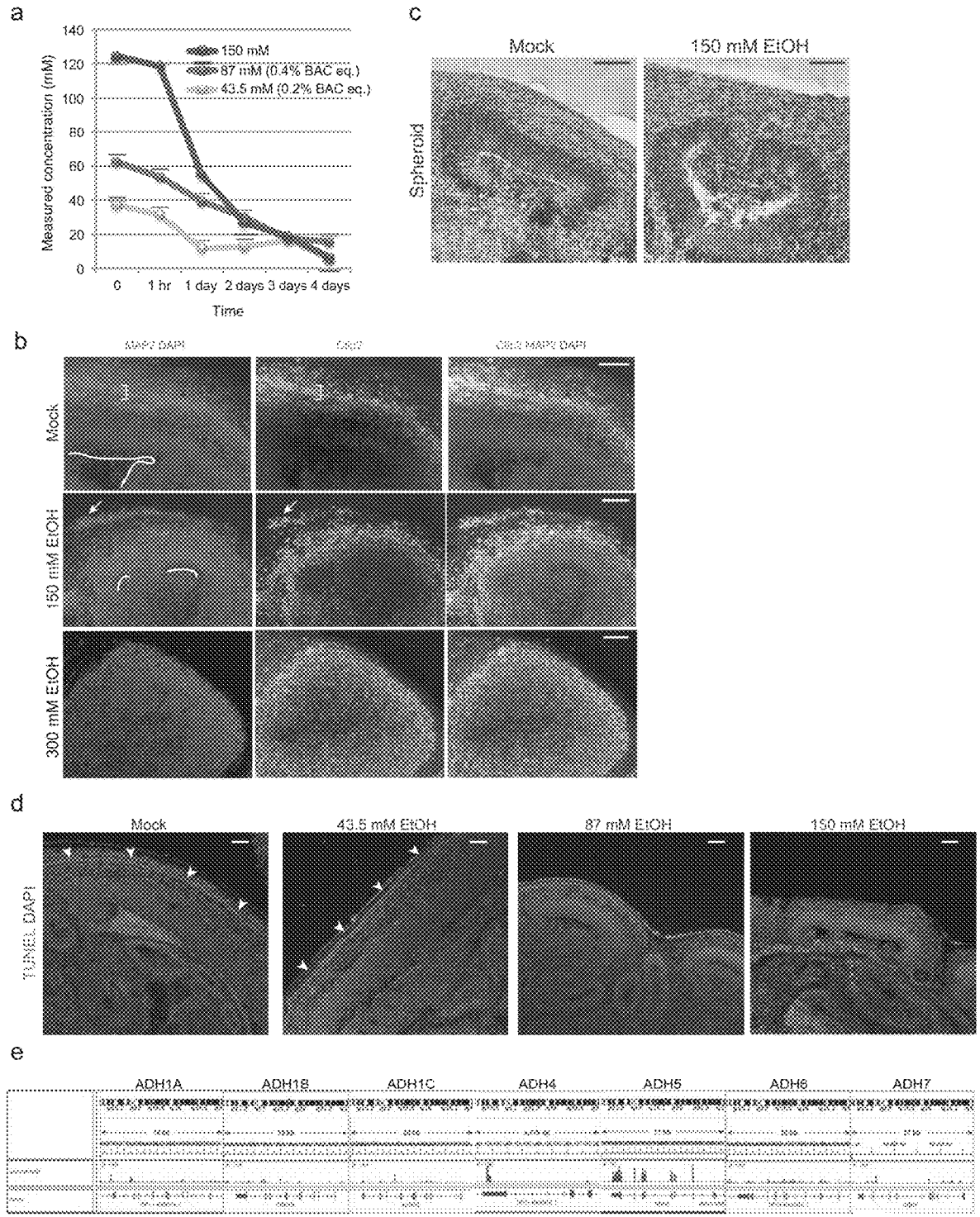

FIG. 21. Ethanol volatility results in a lower than expected concentration and generates specific neuronal migration phenotypes a. Measured concentration in the media at the designated time point for treated H1 enCORs beginning at day 56. Time 0 is immediately after addition of ethanol to the media. BAC eq. refers to the equivalent blood alcohol content % by volume. b. H9 enCORs treated for two weeks beginning at day 46 with a higher dose of 300 mM show completely disorganized cortical lobe with neurons abnormally located in the VZ and the complete absence of recognizable apical surface. 150 mM treated instead show smaller apical surfaces (dashed lines) and no recognizable CP in contrast to water mock (bracket) as well as ectopic neurons (arrow). c. H&E staining of mock water or 150 mM ethanol treated H9 spheroids beginning at day 56 reveals apical surface defects but a failure to detect a CP/neuronal migration defect. d. TUNEL staining in treated and mock water H1 day-70 enCORs after two week treatment, revealing no obvious increase in cell death upon ethanol treatment. Note the presence of the CP (arrowheads) in mock and 47.5 mM ethanol treatments. e. Screen shots of the IGV view of single gene tracks of various alcohol dehydrogenase enzymes in the 60-day enCOR transcriptome. ADH4 and 5 are most highly expressed. Note that ADH4 has previously been described to be involved in metabolism of both ethanol and retinol. Scale bars are 100 µm in all panels.

EXAMPLES

Examples Summary

In order to model more subtle neurological phenotypes, a system was developed that fulfils three important criteria: 1) reliable generation of neural tissues from batch to batch; 2) high purity neural tissues with consistent regional identity; and 3) radial cortical plate organization. By making use of fibrous microscaffolds, it was shown that organoids consistently produce neuroepithelium, eliminating batch-to-batch effects. Furthermore, it was shown that tissues are pure neural and reproducibly generate cerebral cortical structures in all organoids. Finally, it was shown show that the addition of dissolved extracellular matrix allows for the formation of a radialized cortical plate and aligned radial units. This combination of micropatterning and organoid culture in the presence of ECM (FIG. 1a) allows for the study of developmental disorders, including those with neuronal migration defects. Developmental disorders can be modelled based on using cells with genetic defects or by investigating the teratogenic properties of chemical substances or other environmental effects.

Example 1: Preparation of Microfilaments

Poly (lactide-co-glycolide) braided fibers of 10:90 PLGA were obtained commercially as Vicryl sutures (Ethicon). Violet dyed fibers were used to assist in visualization during dispersion and within embryoid bodies. Individual microfilaments were isolated from the braided fiber by mechanical shearing with an angled blade against a stainless steel plate, to obtain filaments of 0.5-1 mm in length, and about 15 µm in diameter. Filaments were then hydrated in embryoid body media and transferred to 15 ml conical tube for storage. Comparative filaments of cellulose were obtained by shaving individual fibers from a Whatman paper. Gelatin fibers were produced by wet-spinning as described previously in Han et al., Adv. Funct. Mater. 2012, DOI: 10.1002/adfm.201201212 without cross-linking.

Example 2: General Outline for Preparing Micropatterned Embryoid Bodies and Cerebral Organoids Embryoid bodies were prepared from single cell suspension of human ES or iPS cells, following accutase treatment. Cells were counted and resuspended in embryoid body media (EB): DMEM/F12 (Invitrogen, cat. #11330-032) and 20% Knockout Serum replacement (Invitrogen, cat. #10828-028), 3% human ES quality batch-tested fetal bovine serum, 1% Glutamax (Invitrogen, cat. #35050-038), 1% MEM-NEAA (Sigma, cat. #M7145), 0.1 mM 2-mercaptoethanol, 4 ng/ml bFGF (Peprotech, cat. #100-18B), and 50 µM Y-27632 ROCK inhibitor (VWR, cat. #688000-5). 18000 cells were added to each well of a 96-well low-attachment U-bottom plate (Sigma, cat. #CLS7007) already containing 5-10 microfilaments in embryoid body media, and media was added to give a final volume of 150 µl per well (FIG. 1a, steps 1 and 2). Based on an average hPSC cell size of 15 µm (measured from hPSC cell suspensions on EVOS microscope, Invitrogen), we calculated that 18000 cells per 5-10 fibers of maximum length 1 mm would result in, at most, 5-10% of cells having direct contact to the fiber.

At day 3, half media was changed with EB media without bFGF and Y-27632. On day 5, EBs were moved with an angled cut P200 tip to 24-well low-attachment plates (Sigma, cat. #CLS3473) with neural induction media (NI) as previously described in WO 2014/090993 A1 (incorporated herein by reference) (FIG. 1a, step 3). Media was changed every other day. On day 11, or when polarized neural ectoderm was visible on the surface, organoids were transferred to droplet of Matrigel as previously described in WO 2014/090993 A1 but kept in NI media (FIG. 1a, transition from step 3 to 4). At day 13 (2 days after Matrigel embedding), media was changed to an improved differentiation media-A (IDMA): 1:1 of DMEM/F12 and Neurobasal (Invitrogen, cat. #21103049), 0.5% N2 supplement (Invitrogen, cat. #17502048), 2% B27-vitamin A (Invitrogen, cat. #12587010), 0.25% insulin solution (Sigma, cat. #I9278-5ML), 50 µM 2-mercaptoethanol, 1% Glutamax, 0.5% MEM-NEAA, and 1% Penicillin-Streptomycin (Sigma, cat. *P0781). Additionally, CHIR 99021 (Tocris, cat. #4423) at 3 µM was added from day 13 to 16. Media was changed every other day and organoids were moved to a spinning bioreactor or orbital shaker as described previously in WO 2014/090993 A1, on day 18 (FIG. 1a, step 5). After moving to the shaker, media was changed every 3-4 days. Shaking speed was calculated based on the throw of the shaker. For a throw of 10 mm, speed was 85 rpm.

Example 3: Addition of Extracellular Matrix (ECM)

At day 20, media was changed to an improved differentiation+A (IDM+A): 1:1 of DMEM/F12 and Neurobasal, 0.5% N2 supplement, 2% B27+vitamin A, 0.25% insulin solution, 50 µM 2-mercaptoethanol, 1% Glutamax, 0.5% MEM-NEAA, 1% Penicillin-Streptomycin, 0.4 mM Vitamin C, and 1.49 g HEPES per 500 ml to control pH levels. Alternatively, media can be pH controlled with further bicarbonate buffering with the addition of 1 mg/ml sodium bicarbonate. At day 40, media was changed to IDM+A with 1 ml dissolved Matrigel per 50 ml media by slowly thawing the Matrigel on ice and addition to cold media to dissolve (FIG. 1a, step 6). A polarized cortical plate was observed.

Variations and Comparative Examples

For treatment with matrix metalloprotease inhibitor GM6001 (Selleck Chemicals S7157), a final concentration of 3 μM was added beginning on day 30. For laminin treatment, 35 μg/ml of pure laminin (Corning 354232) was added beginning on day 40, or 45 μl of high concentration laminin/entactin gel (Corning 354259) was dissolved per 5 ml media, to obtain a protein concentration comparable to final concentration of Matrigel as obtained above.

Comparative cortical spheroids were generated as described previously in Pasca et al., Nature Methods 12, 671-678 (2015). Briefly, H9 feeder-free cells were dissociated with EDTA and intact colonies were plated in a low-attachment 6 cm dish in hES media containing drugs as detailed in the published protocol. On day 6, media was changed to Neural Media and addition of growth factors was performed with the timing described in the protocol. Forebrain SFEBq organoids were generated as described previously in Kadoshima et al., Proc. Natl. Acad. Sci. U.S.A. 110, 20284-20289 (2013). Briefly, iPS cells were dissociated to single cells and 9000 cells plated per low attachment u-bottom well in cortex differentiation media containing small molecules as described in the published protocol. Media changes were performed as described and on day 19 the tissues were moved to DMEM/F12+N2 based media with subsequent addition of FBS, heparin and Matrigel on day 35 as described. B27 was included starting at day 70, along with increased Matrigel exactly as described. For ethanol treatments, 100% ethanol was added to achieve the desired final concentration or an equal volume of water to highest volume of ethanol was used as control mock treated. These concentrations are higher than physiological levels but given the volatility of ethanol, this has been shown to be the most effective in eliciting an effect in neurons in vitro. Ethanol concentrations in the media were measured using the colorimetric ethanol concentration assay (Abcam) according to manufacturer's instructions. A base line measurement was taken for media before ethanol addition, which was subtracted from subsequent measurements. Acetaldehyde treatment was performed with 200 μM final concentration, a concentration found in serum during ethanol intoxication. Treatment with media lacking retinols was performed with the IDM+A media recipe except that B27-A was used. Rescue with retinoic acid was performed with 1 μM final concentration of all-trans retinoic acid. The media was changed with new media containing fresh treatments every 3-4 days.

Example 4: Histological and Immunohistochemical Analysis

Organoids were fixed in 4% paraformaldehyde for 20 min at room temperature and washed with PBS three times for 10 min each at room temperature before allowing to sink in 30% sucrose at 4° C. The tissues were embedded and sectioned and stained as described in Lancaster et al. Nature Protocols 9, 2329-2340 (2014). Primary antibodies used were: Brachyury (R&D Systems AF2085, 1:200), mouse anti-N-Cadherin (BD 610920, 1:500), mouse anti-E-Cadherin (BD 610182, 1:200), goat anti-Sox17 (R&D systems AF1924, 1:200), rabbit anti-Laminin (Sigma L9393, 1:500), rabbit anti-Tbr1 (Abcam ab31940, 1:300), chicken anti-Tbr2 (Millipore AB15894, 1:100), mouse anti-Map2 (Chemicon MAB3418, 1:300), rat anti-Ctip2 (Abcam, ab18465, 1:300), rabbit anti-Arl13b (Proteintech 17711-1-AP, 1:300), mouse anti-phospho-Vimentin (MBL International D076-35, 1:250), rabbit anti-Emx1 (Sigma HPA006421, 1:200), rabbit anti-FoxG1 (Abcam ab18259, 1:200), mouse anti-Reelin, (Millipore MAB5366, 1:200), mouse antiCalretinin (Swant 6B3, 1:100), rabbit anti-Satb2 (Abcam ab34735, 1:100), rabbit anti-Otx2 (Abcam ab21990, 1:200), goat anti-En2 (Santa Cruz Biotechnology sc-8111, 1:50), goat anti-DCX (Santa Cruz Biotechnology sc-8066, 1:300), mouse anti-CSPG (Abcam ab11570, 1:100), rabbit anti-Cux2 (Abcam ab130395, 1:200), mouse anti-Nestin (BD G11658, 1:500). DAPI was added to secondary antibody to mark nuclei. Secondary antibodies labeled with Alexafluor 488, 568, or 647 (Invitrogen) were used for detection. TUNEL staining was performed using the In Situ Cell Death Detection Kit-Fluorescein (Roche) according to manufacturer's instructions. For histological analysis, sections were stained for hematoxylin/eosin followed by dehydration in ethanol and xylene and mounting in permount mountant media. Images were acquired on a confocal microscope (Zeiss LSM 710 or 780). Statistical analysis of quantifications performed from imaging data was performed using Student's t-test for significance.

Example 5: Electroporation of Organoids and Live Imaging

Electroporation of pmax-GFP construct (Lonza) or an integrating farnesylated GFP was performed as described previously in Lancaster et al. Nature 501, 373-379 (2013). For pmax-GFP, 4 μl of 250 ng/μl were injected into several ventricular spaces. The integrating farnesylated GFP was generated by cloning the CAG promoter into the pT2/HB transposon plasmid (a gift from Perry Hackett, Addgene plasmid #26557) followed by inserting a GFP construct with farnesyl sequence (pT2-Cag-fGFP). Sleeping beauty transposase plasmid was generated by cloning the SB100X transposase (pCMV(CAT)T7-SB100, Addgene plasmid #34879) into the pCAGEN plasmid with CAG promoter (Addgene plasmid #11160). Electroporation was performed by injecting 80 ng/μl pT2-Cag-fGFP and 240 ng/μl pCAGEN-SB100X. For neuronal morphology analysis, samples were fixed 36 days after electroporation of the fGFP and analysed by sectioning and immunohistochemistry as above.

Slice culture was performed by embedding samples in 3% low-melting point agarose and sectioned on a vibratome to collect 300 μm sections on the air side of organotypic culture inserts (Millipore) inside a 3 cm coverglass bottomed dish containing 1 ml serum-supplemented media: DMEM, 10% FBS, 0.5% (w/v) glucose, supplemented with penicillin-streptomycin. Sections were cultured for 1 hour before changing the media to serum-free media: DMEM, 1:50 B27+A, 0.5% (w/v) glucose, glutamine and penicillin-streptomycin. The slices were left to flatten and equilibrate overnight before imaging over several days using a Zeiss 780. For this long-term imaging, addition of HEPES (25 mM final) was performed for added buffering.

Calcium imaging was performed as previously described in Lancaster et al., Nature 501, 373-379 (2013) using Fluo-4 Direct (Life Technologies) on slice cultures. Frames were analyzed in ImageJ and progressive increasing intensity was corrected by using the Bleach Correction function on frames in reverse order. Individual cell traces were performed by outlining specific cells as regions of interest and mean grey value measured. ΔF/F was calculated as follows: (mean grey value−minimum grey value)/minimum grey value.

Example 6: RT-PCR Analysis of Gene Expression

Three organoids for each condition were collected in Trizol reagent (Thermo Fisher) and RNA isolated according to manufacturer. DNA was removed using DNA-Free kit (Ambion) and reverse strand cDNA synthesis was performed using Superscript III (Invitrogen). PCR was performed using primers for a panel of pluripotent and germ layer identities (R&D systems, SC012).

Example 7: RNA-Seq Analysis

Three individual H9 organoids for each condition were collected at the indicated time points. RNA was isolated using Arcturus PicoPure RNA Isolation Kit (Thermo Fisher Scientific, cat. #KIT0204) (20 days timepoint) or Trizol Reagent (Thermo Fisher Scientific, cat. #15596018) (60 days timepoint) according to the manufacturer's instructions. RNA concentration and integrity was analysed using RNA 6000 Nano Chip (Agilent Technologies, cat. #5067-1511). RNA was enriched for mRNA using Dynabeads mRNA Purification Kit (Thermo Fisher Scientific, cat. #61006). Libraries were prepared using NEBNext Ultra Directional RNA Library Prep Kit for Illumina (NEB, cat. #E7420L). Barcoded sampies were multiplexed and sequenced 50 bp SE on a HighSeq2500 (Illumina). Sample preparation and sequencing was performed at the VBCF NGS Unit (www.vbcf.ac.at). Data will be submitted to GEO and accession numbers provided.

The strand specific reads were screened for ribosomal RNA by aligning with BWA (v0.6.1) against known rRNA sequences (RefSeq). The rRNA subtracted reads were aligned with TopHat (v1.4.1) against the *Homo sapiens* genome (hg38) and a maximum of 6 missmatches. Maximum multihits was set to 1 and InDels as well as Microexonsearch was enabled. Additionally, a gene model was provided as GTF (UCSC, 2015_01, hg38). rRNA loci are masked on the genome for downstream analysis. Aligned reads are subjected to FPKM estimation with Cufflinks (v1.3.0). In this step bias detection and correction was performed. Furthermore, only those fragments compatible with UCSC RefSeq annotation (hg38) of genes with at least one protein-coding transcript were allowed and counted towards the number of mapped hits used in the FPKM denominator. Furthermore, the aligned reads were counted with HTSeq (0.6.1p1) and the genes were subjected to differential expression analysis with DESeq2 (v1.6.3).

GO term enrichment analysis was performed on genes with an adjusted p value <0.1 and absolute log 2fc value >1 in at least one of the conditions (20 day or 60 day, spheroid or enCOR). Each set of differentially expressed genes were analysed using Pantherdb.org for GO Slim biological process enrichment and fold enrichment for terms as well as multi-test corrected P-value (plotted as −log 10(Pvalue) were plotted.

For hierarchical cluster analysis, genes were reorganized based on their similarity of log 2fc values by means of Ward hierarchical clustering using heatmap.2 of the gplots package in R. Cutree function gave the 7 clusters used for subsequent GO term analysis. Gene lists were fed into Pantherdb.org for GO Biological Process Complete, yielding a large list of redundant terms. Therefore, in order to remove redundancy, we narrowed the list using GO Trimming and a cutoff of terms with fold enrichment value >2 yielding the list of GO terms that were plotted by fold enrichment value and −log 10(Pvalue). Individual tracks were visualized using Integrative Genomics Viewer IGV 2.3.68 (Broad Institute).

For comparison to Allen BrainSpan human transcriptome dataset, the RPKM expression values of Brainspan were downloaded (www.brainspan.org/static/download.html). FPKM values were filtered for differential expression in the 60d time-points (padj<0.1) and joined with Brainspan via the gene symbols. The similarity of expression was compared by the rank of the expressed gene via Spearman correlation. The heatmap of Spearman coefficient for each region at fetal time points was generated using heatmap.2 without hierarchical clustering. The list was manually ordered according to anterior-posterior regional position and separated into four developmental stages.

Figure 4:
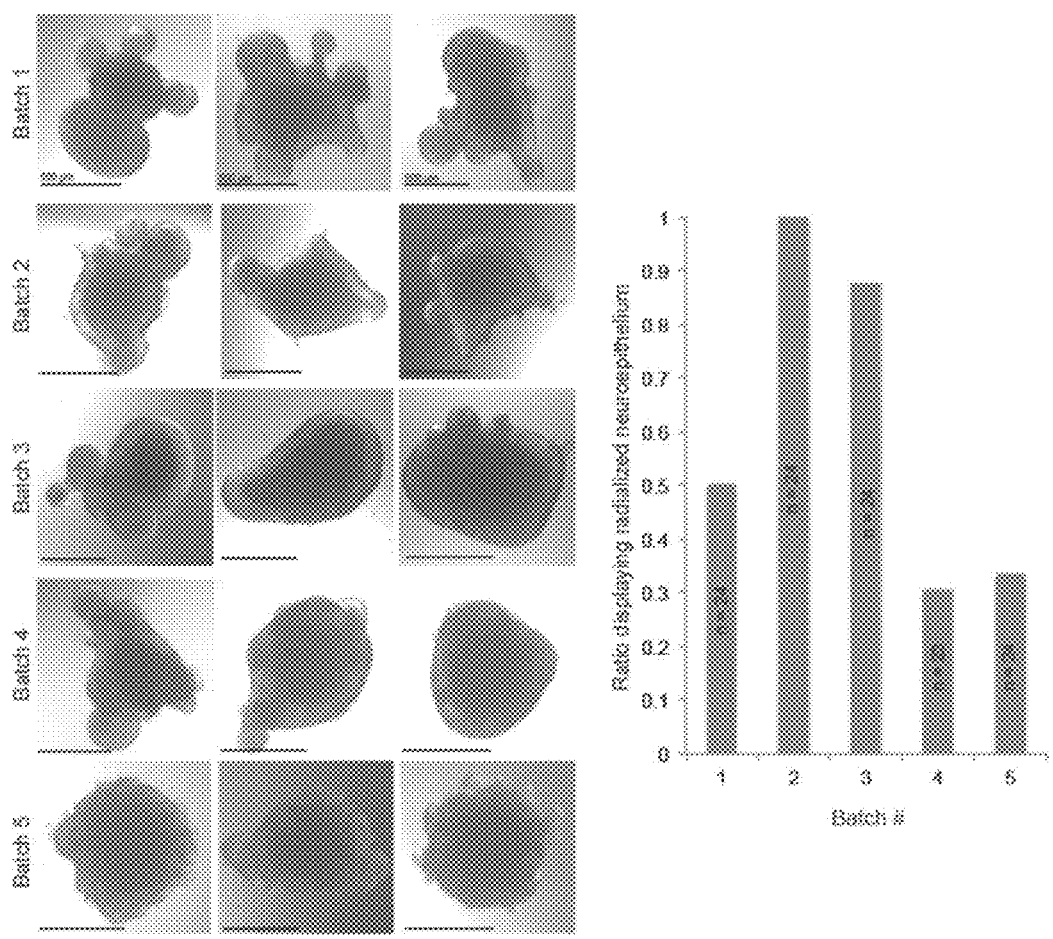
FIG. 4. Bright field images of five independent batches of spheroid organoids showing the degree of variability in generation of polarized neuroectoderm and quantification at the right.
Figure 5:
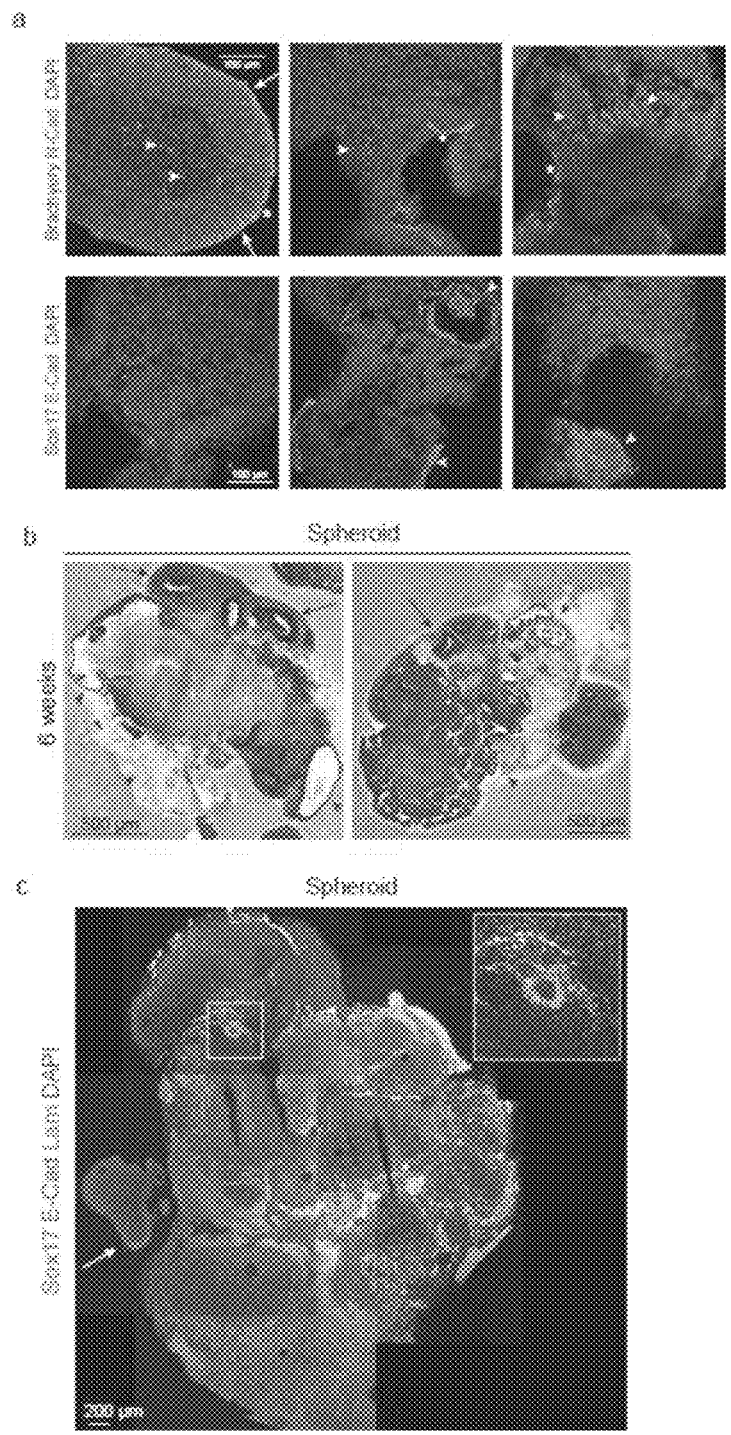
FIG. 5. a. Immunohistochemical staining of day 10 spheroid EBs for the germ layer markers Brachyury for mesoderm, N-Cadherin for neural ectoderm, Sox17 for endoderm and E-Cadherin for non-neural epithelium. Note the polarized neural epithelia (arrows) displaying the apical domain on the surface (white asterix) while some mesoderm or endoderm identities (arrowheads) are visible. b. Haematoxylin and eosin staining of spheroid organoids showing lobes of brain tissue (arrows) but also nonneural regions such as fluid-filled cysts and fibrous regions (arrowheads). Immunohistochemical staining of a spheroid organoid reveals occasional endoderm (Sox17+, inset) and nonneural epithelia (arrow) even at a later time point of 40 days.

Example 8: Micropatterned Cerebral Organoids Consistently Produce Organized Neuroepithelium In order to identify the source of batch-to-batch variability in previous cerebral organoid preparations, five independent comparative batches at various time points were examined. The earliest appearance of batch-to-batch effects could be seen during neural induction. Specifically, there were varying efficiencies of generation of polarized neural ectoderm that ranged from 30% to 100% of organoids per batch (FIG. 4). Notably, batches with low rates of neural ectoderm formation instead contained tissues with other morphologies suggesting the presence of nonneural ectoderm, or other germ layer identities. Therefore immunohistochemical staining of early cerebral organoids was performed for various germ layers. Optimal organoids displayed a well-organized and apicobasally polarized neural epithelium around the surface of the organoid, with only sparse cells staining positive for other germ layers (FIG. 5a). However, suboptimal organoids displayed less well-organized architecture with a greater extent of staining for other cell identities, such as endoderm and mesoderm. Additional histological sectioning and staining at later stages identified a number of tissues with non-neural morphologies in addition to neural regions, such as putative cartilage, mesenchyme and squamous epithelia (FIG. 5b). Furthermore, immunohistochemical staining revealed the existence of occasional definitive endoderm, as well as other nonneural E-cadherin positive regions (FIG. 5c). These findings show variability in the efficiency of neural induction, with some batches giving rise to other germ layers and/or non-neural ectoderm.

Figure 6:
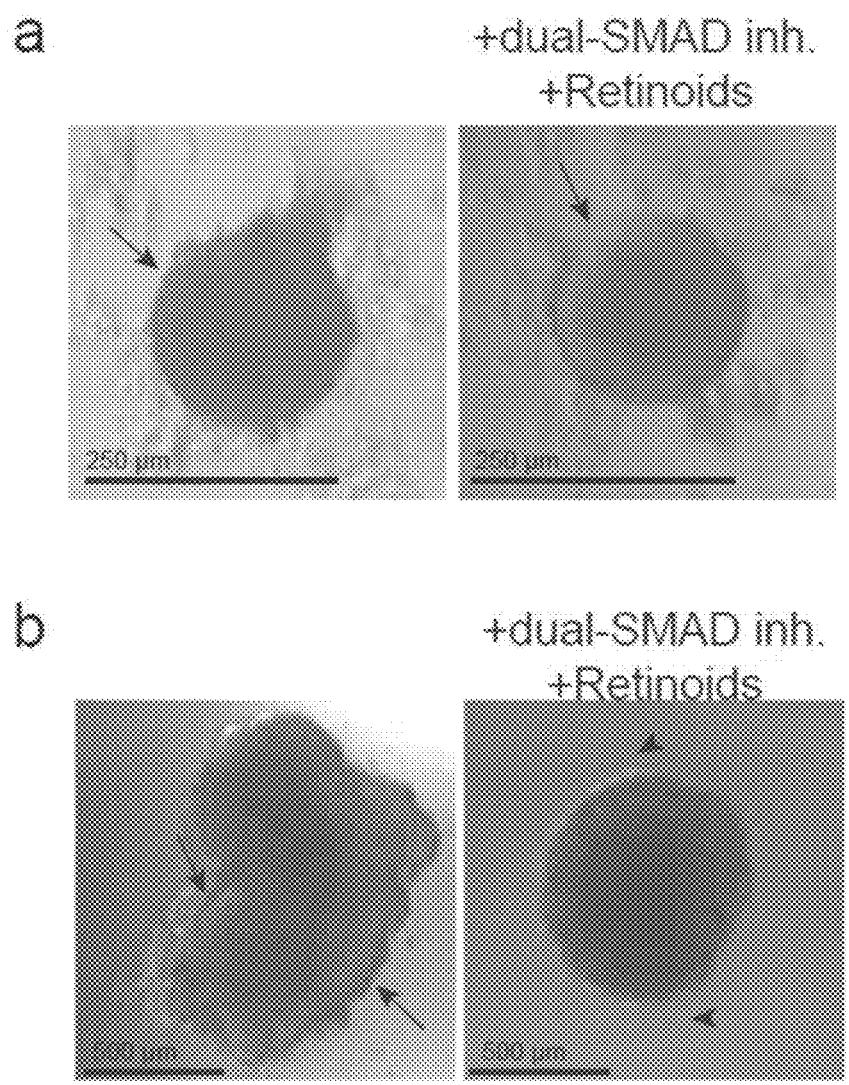
FIG. 6. a. Bright field images showing that treatment of spherical EBs with dual-SMAD inhibition and retinoids improves early (day 3) morphology with a greater extent of surface clearing. b. Bright field imaging following matrigel embedding, however, reveals that treated EBs do not form large buds of neural epithelium instead generating numerous small rosettes and already generating neurons.

A very high efficiency neural induction and cerebral cortical regionalization can be achieved with dual SMAD inhibition and retinoids. Therefore it was tested whether this approach could improve induction efficiency in the context of organoids, by culturing the organoids at embryoid body (EB) stage in a media composed of retinoids and dual SMAD inhibitors (dorsomorphin and SB-431542). EBs cultured in this combination showed dramatically increased clearing at day 4, indicative of ectoderm formation (FIG. 6a). However, upon embedding in Matrigel, the treated organoids failed to produce buds of neuroepithelium, instead displaying small rosette-like structures with neural processes (FIG. 6b). The finding that dual SMAD inhibition and retinoid signalling could dramatically increase neuroectoderm formation but at the expense of neural tissue morphology suggests that non-neural tissues may be important for the formation of complex morphologies seen in cerebral organoids. Optimal batches of organoids displayed larger quantities of polarized neuroectoderm were observed (FIG. 5a). The ratio of neural to non-neural tissue could still be improved.

Figure 1:
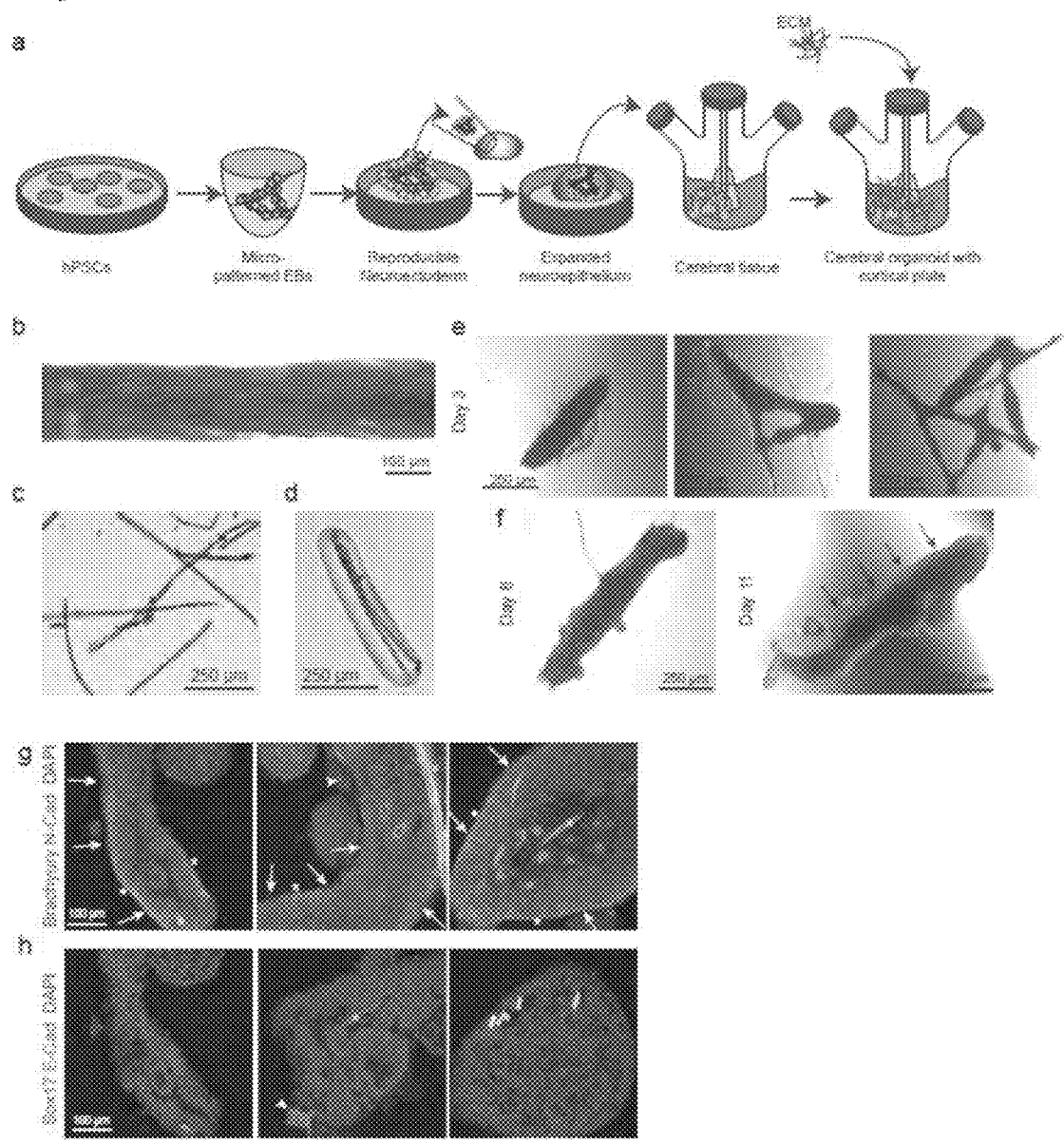
FIG. 1. a. Schematic of the method for generating microfilament patterned embryoid bodies (EBs) and their subsequent growth as cerebral organoids with cortical plate. b. Bright field image of the intact braided PLGA (poly(lactic-co-glycolic acid)) fiber. c. Bright field image of isolated microfilaments. d. Hydrated microfilaments within a droplet of EB medium. e. Three examples of micropatterned EBs at day 3 of the protocol. Note the elongated and sometimes complex arrangement. f. Micropatterned EBs at later stages, during the neural induction phase, showing clearing along the edges and polarized neural ectoderm (arrows). g, h. Immunohistochemical staining of day 10 micropatterned EBs for the germ layer markers Brachyury for mesoderm (g), N-Cadherin for neural ectoderm (g), Sox17 for endoderm (h) and E-Cadherin for non-neural epithelium (h). Note the prevalence of polarized neural epithelia (arrows) displaying the apical domain on the surface (white asterix) with only occasional mesoderm or endoderm identities (arrowheads). The microfilament can be seen as an autofluorescent rod (yellow asterix).

The inventive cerebral organoid protocol begins similar as spheroid EB formation (FIG. 1). It is hypothesized that since neural ectoderm forms on the outside of these tissues during neural induction, a sphere could limit the surface area to volume ratio and potentially allows a greater extent of non-neural tissue formation. In order to increase the surface area of organoids a micropatterning scaffold was used to shape the early EB stage organoids and elongate the primitive neuroectoderm. This micropatterning gives rise to microfilament engineered cerebral organoids (also referred to as enCORs herein).

Figure 12:
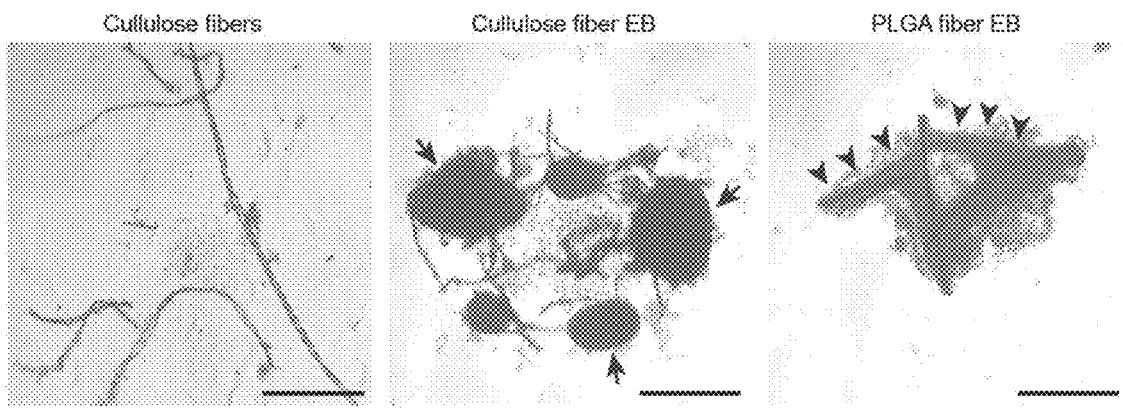
FIG. 12. Cellulose fibers with similar dimensions (left panel) fail to form elongated EBs (middle panel) compared with the PLGA based fibers (arrowheads) at day 3 with H9 cells, and instead remain as clumps (arrows) only partially attached to the fibers. Scale bars: 500 μm in FIG. 4., FIG. 12., 250 μm in FIG. 1c., d., e., 100 μm in FIG. 1b.

Fibrous microscaffolds are a widely used system for providing patterned scaffolds in tissue engineering, allowing for diverse shapes that can be seeded with cells and even implanted in vivo. However, because EBs are generated with relatively few cells (thousands rather than the millions typically used in tissue engineering applications), and the goal here was to provide an individual micrometer scale guide, a method was devised for mechanical dispersion of individual filaments from braided fibers (FIG. 1b-d). The effect of addition of 5-10 microfilaments of glycolide/lactide copolymer, a material that can be absorbed by means of hydrolysis over the course of 8-10 weeks when implanted in living tissue, was tested. The microfilaments were collected in a random configuration at the bottom of a low-attachment round-bottom microwell and seeded with 18,000 hPSCs, a ratio that results in only 5-10% of cells in direct contact with the filament. The hPSCs attached evenly along the length of PLGA microfilaments thereby forming a plurality of cells of an oblong or longish arrangement (FIG. 1e). Similar results were observed with gelatin microfilaments. In contrast, microfilaments composed of cellulose instead resulted in round aggregates only partially attached to the fibers (FIG. 12) suggesting filament material is important for adherence of cells along the entire length.

Figure 7:
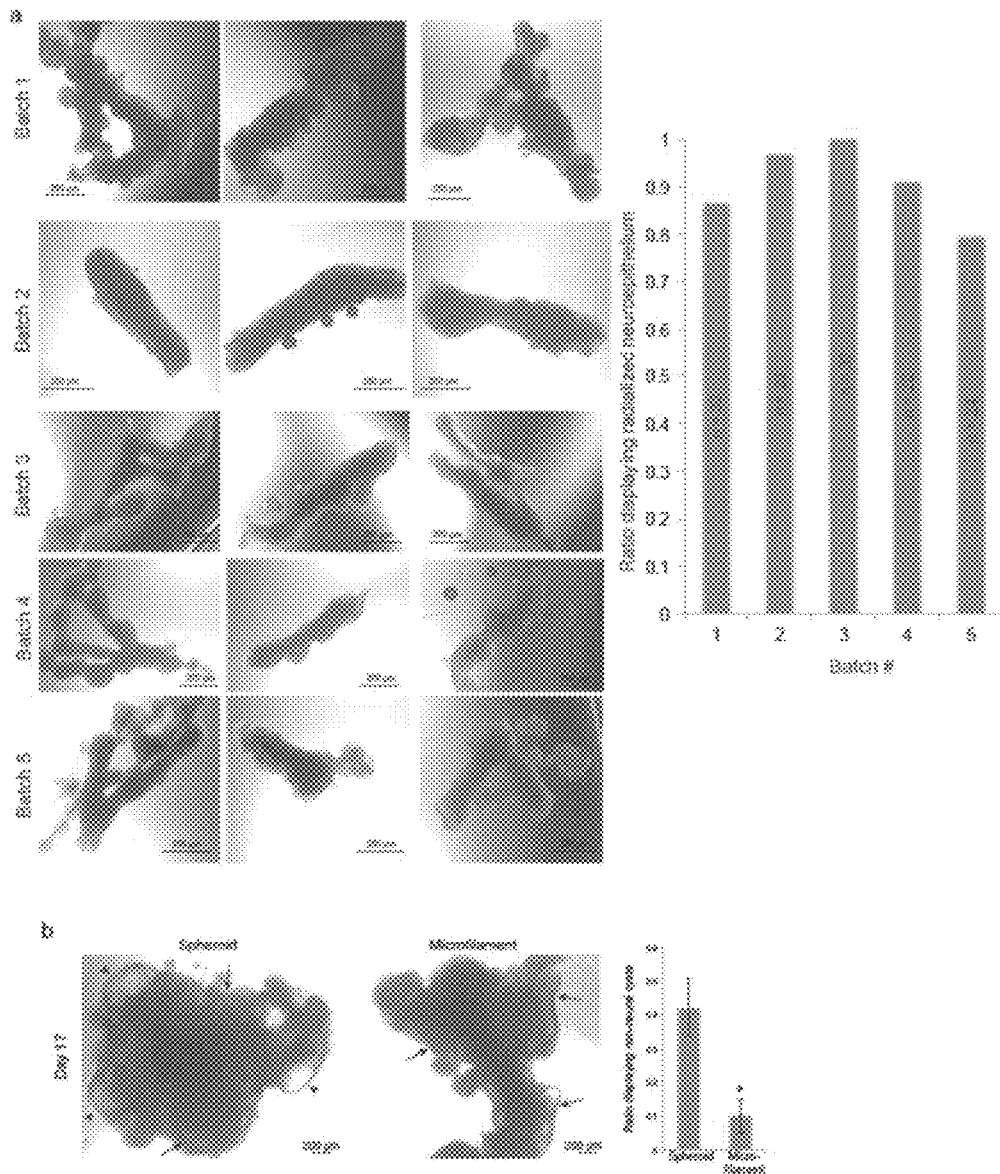
FIG. 7. a. Bright field images of five independent batches of microfilament patterned organoids showing reduced variability in generation of polarized neuroectoderm and quantification at the right. b. Bright field images several days following matrigel embedding showing the prevalence of non-neural cysts in unpatterned organoids compared with microfilament patterned organoids, and quantification at the right.
Figure 13:
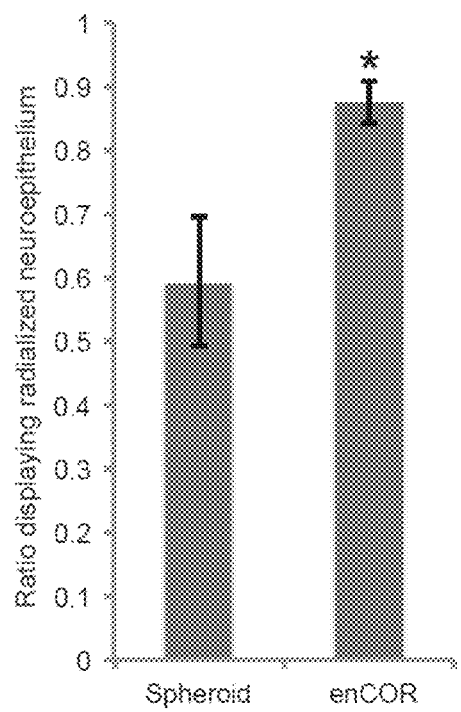
FIG. 13. Quantification of the mean ratio of spheroids or enCORs displaying neuroepithelium. *P<0.05, Student's t-test, n=7 independent batches each. Scale bars: 250 μm.

When microfilaments were added along with hPSCs to low-attachment round-bottom wells, the fibrous scaffolds accumulated at the bottom of the well and were seeded with cells in a random configuration allowing for the successful formation of EBs with elongated morphologies (FIG. 1e). The elongated EBs progressively grew in size and exhibited clearing along the edges with eventual formation of polarized neural ectoderm, much like spheroid EBs; however, the neural ectoderm was dramatically elongated (FIG. 1f) and the efficiency of formation of neuroectoderm was much improved with consistent neural induction in all independent preparations examined (FIG. 7, FIG. 13). These data point to the ability of microfilament scaffolds to more reliably generate radialized neural ectoderm.

Figure 14:
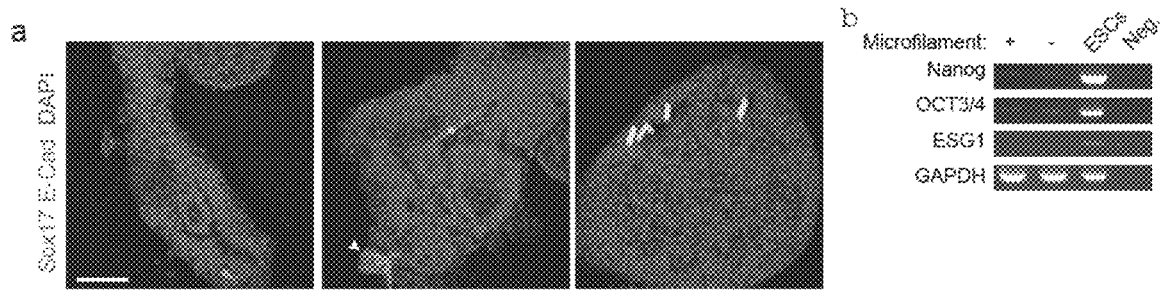
FIG. 14. Decreased formation of non-neural tissue in enCORs a. Immunohistochemical staining of day 10 H9 enCOR EBs for Sox17 for endoderm and E-Cadherin for non-neural epithelium reveals only occasional cells (arrowhead) with these non-neural identities. The microfilament can be seen as an autofluorescent rod (yellow asterisk). b. RT-PCR for markers of pluripotency in 20-day H9 microfilament enCORs or spherical organoids. Embryonic stem cells (H9 cells) are positive control and Neg. is the water control. Scale bars: 100 μm in FIG. 14 a., FIG. 5a., 200 μm in FIG. 7b, FIG. 5c.

Due to the elongated and, at times, complex configurations of micropatterned EBs, surface area to volume was increased, leading to the hypothesis that resulting early stage organoids would display increased polarized neuroepithelium and decreased quantities of other germ layer identities. In order to test this hypothesis, we performed immunohistochemical staining of early stage micropatterned EBs for various germ layer identities and observed more consistent generation of elongated polarized neuroepithelium with concomitant decreased amounts of endoderm and mesoderm identities (FIG. 1g, h). This was in contrast with spherical organoids, which often displayed non-ectodermal identities, especially in suboptimal organoids (FIG. 5a). Furthermore, expression analysis for pluripotency and germ layer markers by RT-PCR, revealed a decrease in non-neural identities in enCOR organoids (FIG. 8c and FIG. 14b). As organoids developed, enCORs displayed fewer morphological features of other germ layers such as the formation of early fluid-filled cysts (FIG. 7b). Furthermore, enCORs contained large lobes of brain tissue (FIG. 2c) but only few regions expressing markers for endoderm and non-neural epithelia (FIG. 5c), in contrast to spherical organoids. These findings suggest that reproducible generation of elongated neural ectoderm can be accomplished by mechanical means rather than through the addition of patterning growth factors.

Example 9: Consistent Generation of Large Cortical Regions with Dorsal Identity

Figure 2:
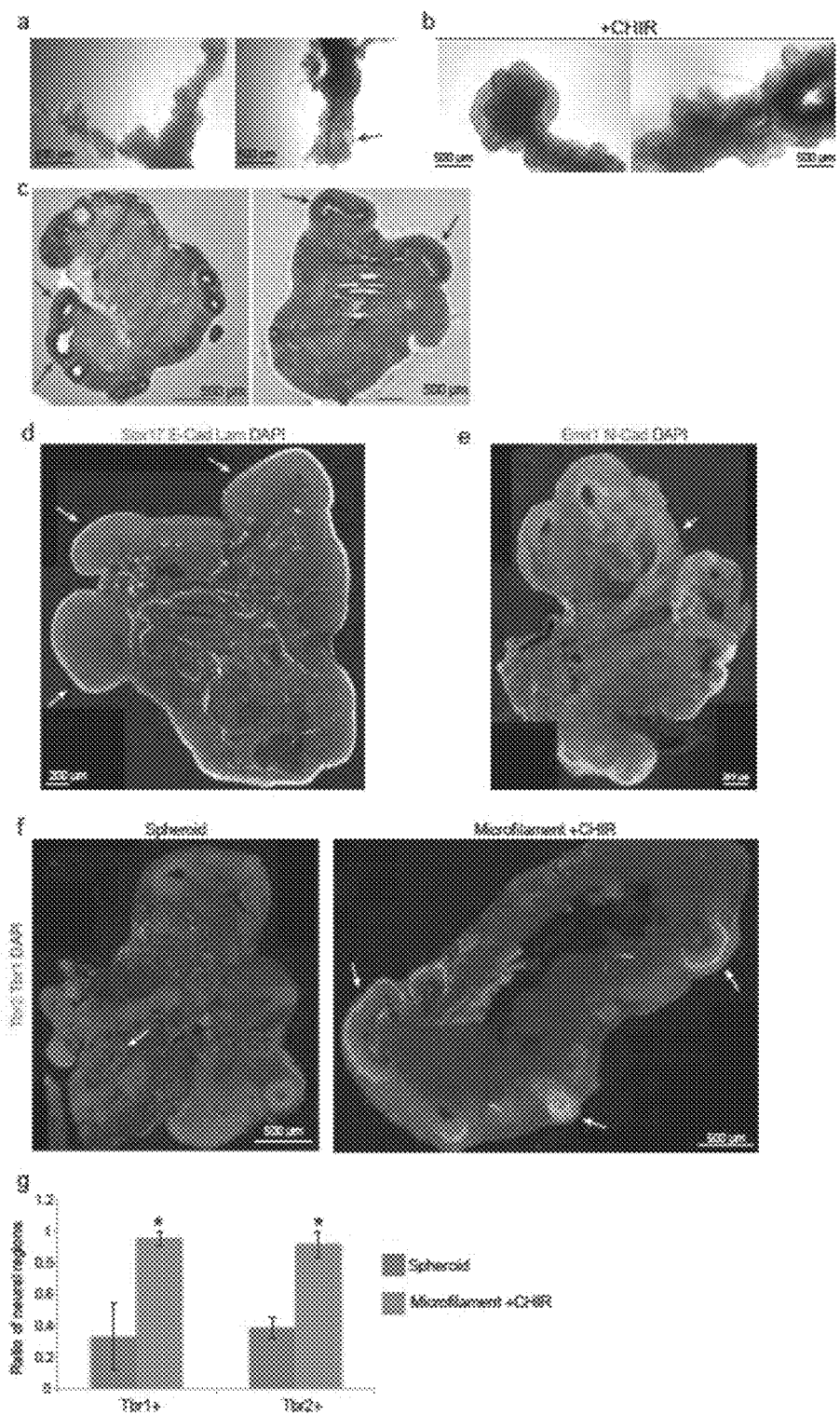
FIG. 2. a. Bright field image of micropatterned organoids shortly after matrigel embedding, displaying numerous small buds of neuroepithelium (arrows). b. Embedded micropatterned organoids following three days of treatment with CHIR. Note the larger, more continuous buds of neuroepithelium. c. Histological section stained with haematoxylin and eosin showing pure neural tissue and many large continuous lobes of brain tissue (arrows). d. Immunohistochemical staining shows an absence of nonneural identities (Sox17 and E-Cadherin) and several large lobes of brain tissue (arrows). e. Immunohistochemical staining for the dorsal cortical marker Emx1 (green) and the neural identity marker N-Cadherin (red) reveals much of the tissue is composed of dorsal cortical brain regions. f. Staining for dorsal cortical markers Tbr2 and Tbr1 identifies all large lobes of brain tissue within microfilament patterned organoids treated with CHIR to be dorsal cortex (arrows). Organoids that were not patterned (spheroid) show much fewer dorsal regions and large brain regions that lack this identity. g. Quantification of the ration of lobes of brain tissue that were positive for Tbr1 or Tbr2 in spheroid or microfilament patterned organoids. *P<0.05, Student's t-test.

Upon Matrigel embedding, micropatterned brain organoids displayed extensive neuroepithelial budding along the length of the previously extended polarized neuroectoderm (FIG. 2a). In contrast to the continuous neuroectoderm that was present prior to embedding which displayed the apical surface directed outwards, neuroepithelial buds were fully enclosed epithelium around a central lumen with the apical surface directed inwards. However, due to the nature of this epithelial reorganization, which in many ways mimics neural tube closure, the resulting neural tube-like epithelia were less continuous.

Figure 15:
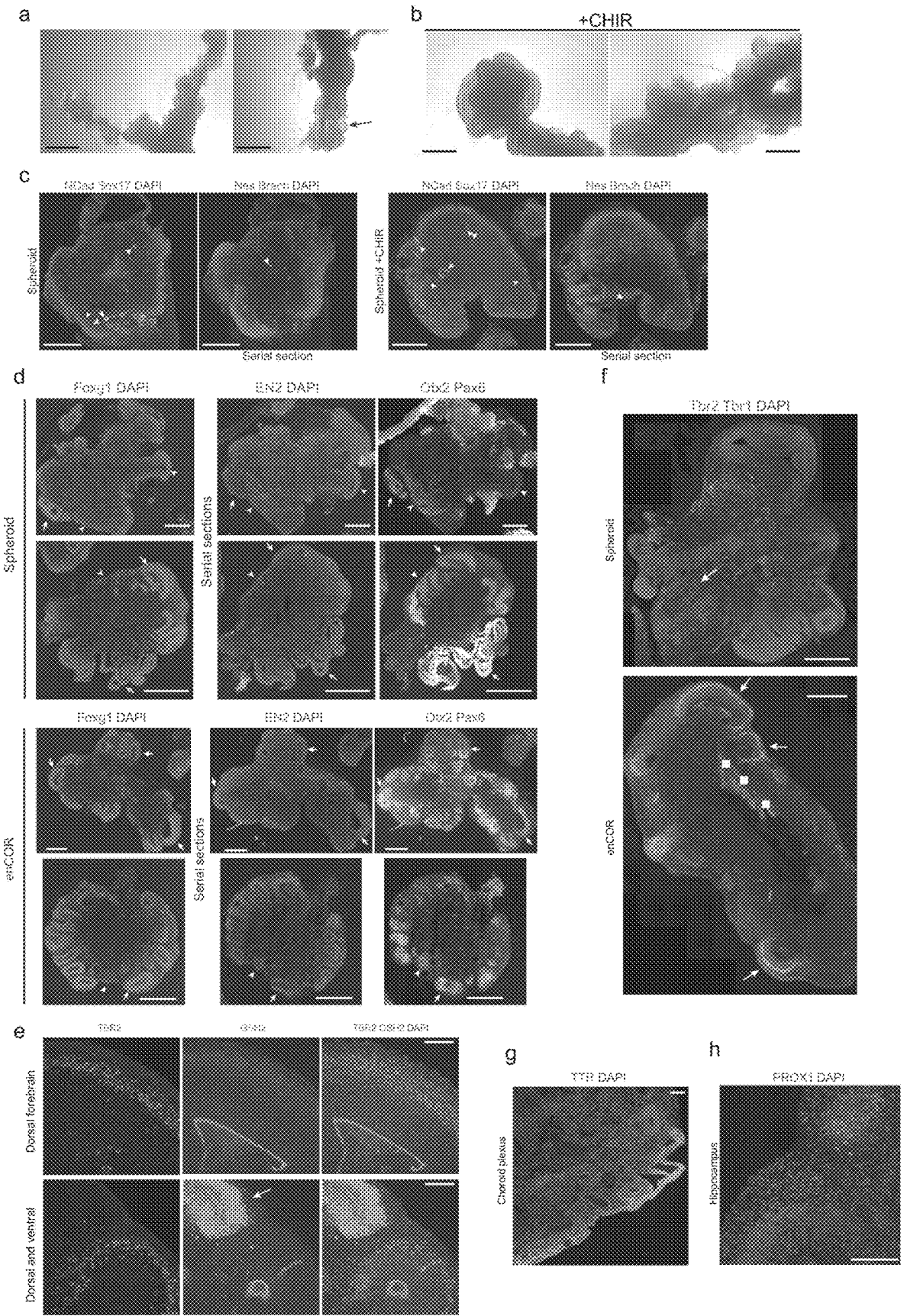
FIG. 15. Reproducible formation of forebrain tissue in enCORs a. Bright field image of H9 microfilament organoids shortly after Matrigel embedding (day 19), displaying numerous small buds of neuroepithelium (arrows). b. Embedded H9 microfilament organoids at day 19, following three days of treatment with CHIR. Note the larger, more continuous buds of neuroepithelium. c. Staining of day 40 H1 spheroids for neural (N-Cadherin or Nestin) and non-neural identities (Sox17 or Brachyury) revealing similar quantities of these identities with and without a three day pulse of CHIR. d. Representative images of stained sections of day 40 H9 organoids used for quantification shown in FIG. 1f. Individual lobes can be recognized as radially oriented, polarized neuroepithelium surrounding a fluid filled ventricle. Serial sections were stained for the indicated markers. Forebrain tissues (white arrows) are Foxg1+ and exhibit fainter Otx2 signal, midbrain tissue (white arrowhead) exhibits strong immunoreactivity for Otx2 and lack other markers, and cerebellar tissue (yellow arrowhead) exhibits staining for both Otx2 and En2, while En2 single positive regions are hindbrain. Foxg1+ regions showing strong Pax6 staining are dorsal forebrain. However, Pax6 also stains other regions such as that marked by the yellow arrow, which is likely spinal chord, as it does not exhibit staining for the other markers. e. Staining for the ventral forebrain marker Gsh2 and the dorsal marker Tbr2 in H9 enCORs at day 40 reveals the presence of both regions of the forebrain. f. Staining of day 40 H9 enCOR brain organoids and spheroids for the markers of dorsal cortex Tbr1 and Tbr2 reveals large lobes of tissue that are dorsal cortex (arrows) in enCORs. Spheroids show much fewer dorsal regions and some large brain regions that lack this identity. g. Staining for the marker of choroid plexus TTR reveals the presence of this region in H9 40-day enCORs h. Staining for the marker of hippocampus Prox1 reweals the presence of this tissue in H9 40-day enCORs. Scale bars: 500 μm in a., b., c., d., f., 100 μm in e., g., h.

Since we were interested in consistently generating large continuous cortical regions, we therefore sought methods to expand these neural tube-like epithelia. Previous in vivo studies have demonstrated the ability of activated Wnt signalling to lead to lateral expansion of cortical neuroepithelium. We therefore tested the effect of adding the GSK3beta inhibitor and Wnt activator CHIR (CHIR99021; stemgent, cat.nr: 04-0004) following neuroepithelial budding. Addition of CHIR led to a dramatic lateral expansion of neuroepithelial tissues and the generation of larger lumens with surrounding continuous neuroepithelium (FIG. 2b). Because Wnt signalling is also an important patterning factor, and we sought to limit the extent of exogenous patterning, we performed also treatment for only a short 3-day pulse. This treatment alone did not influence germ layer induction or overall organoid morphology (FIG. 15c).

We next examined micropatterned organoids at later stages by histological staining which also revealed more consistent generation of large brain regions (FIG. 2c). Furthermore, consistent with the effect of micropatterning on germ layer identity determination, there were fewer regions with non-neural morphologies. This was confirmed by immunohistochemical staining which revealed a reduction of definitive endoderm and non-neural epithelia in micropatterned brain organoids (FIG. 2d), in contrast to spheroid organoids (FIG. 5c).

enCORs with the combination of microfilament and CHIR pulse displayed more consistent formation of Foxg1+ forebrain tissues compared with spheroids, as well as decreased frequency of Otx2+ midbrain and En2+ cerebellar/hindbrain regions (FIG. 8b, 8c, 15d), suggesting more reliable formation of forebrain neural tissue. Consistent with this, enCORs displayed both dorsal and ventral forebrain regions (FIG. 15e) with more frequent large regions that stained positive for dorsal cortical markers Tbr1 and Tbr2 (FIG. 15f). Furthermore, enCORs displayed regions with identity consistent with choroid plexus and hippocampus (FIG. 15g, 15h). Thus, together with late GSK3beta inhibition, micropatterning of cerebral organoids results in reproducible formation of forebrain tissue with little contamination from other germ layers and brain regions.

Figure 16A:
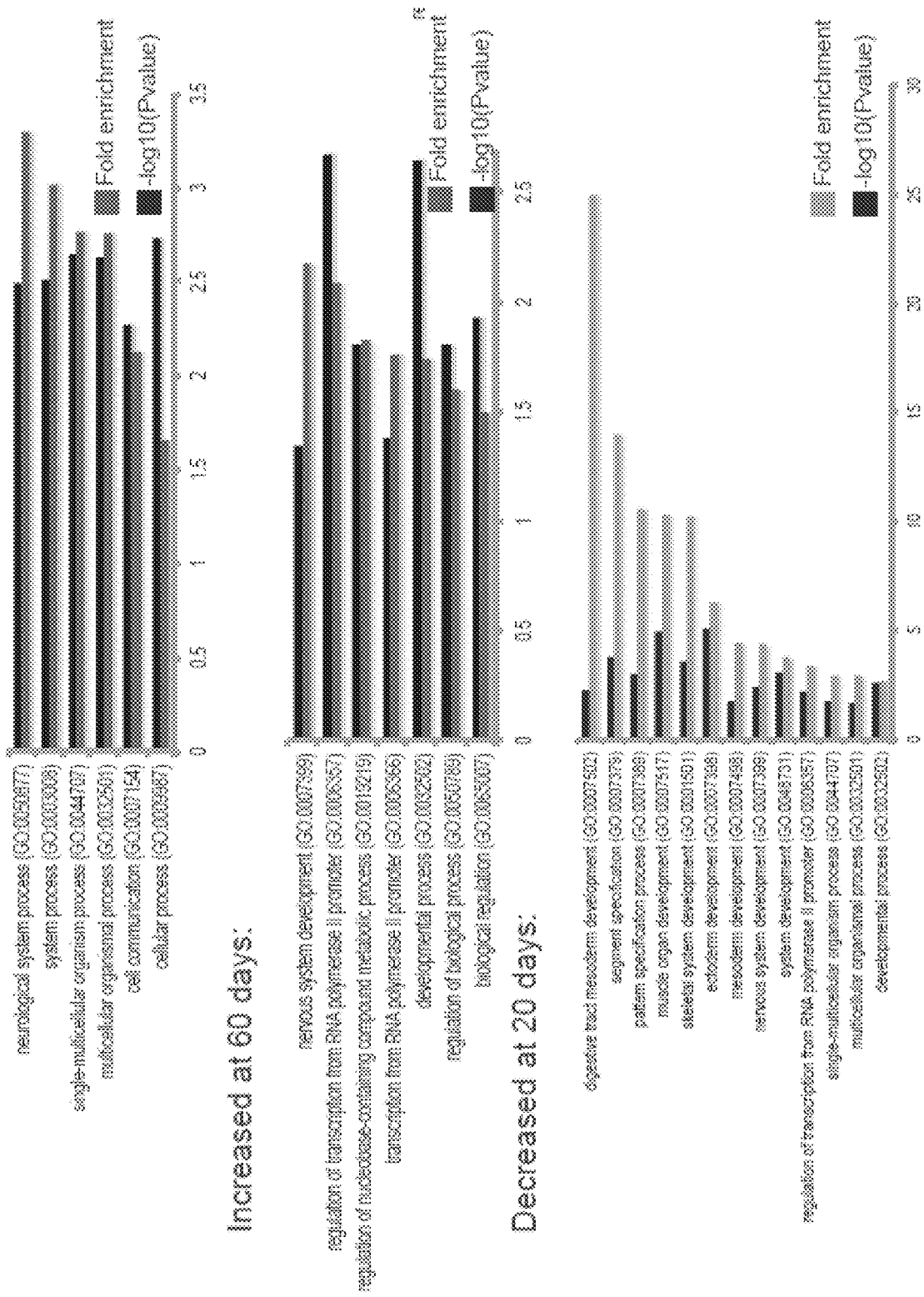
FIG. 16. Transcriptome profiling reveals increased neural identity and preferential formation of forebrain a. Fold enrichment and −log 10(P-value) of GO Slim Biological Process terms for genes increased or decreased in enCORs at 20 and 60 days. b. Heatmap of hierarchical clustering of genes according to log 2fc values at 20 days and 60 days in enCORs versus spheroids. Clusters are marked and GO biological process term summaries of terms identified (FIG. 17) shown at right.
Figure 16:
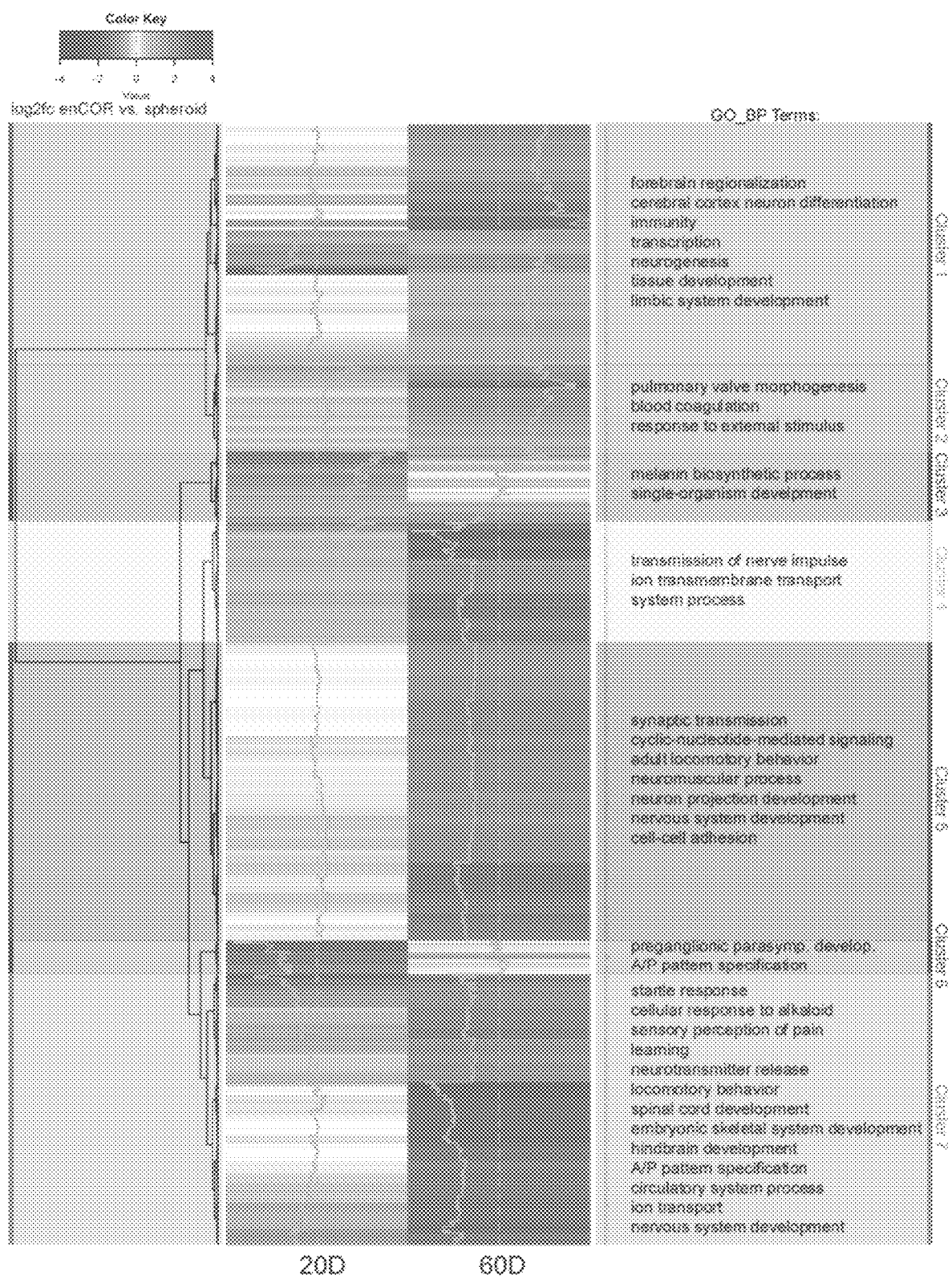
Figure 17:
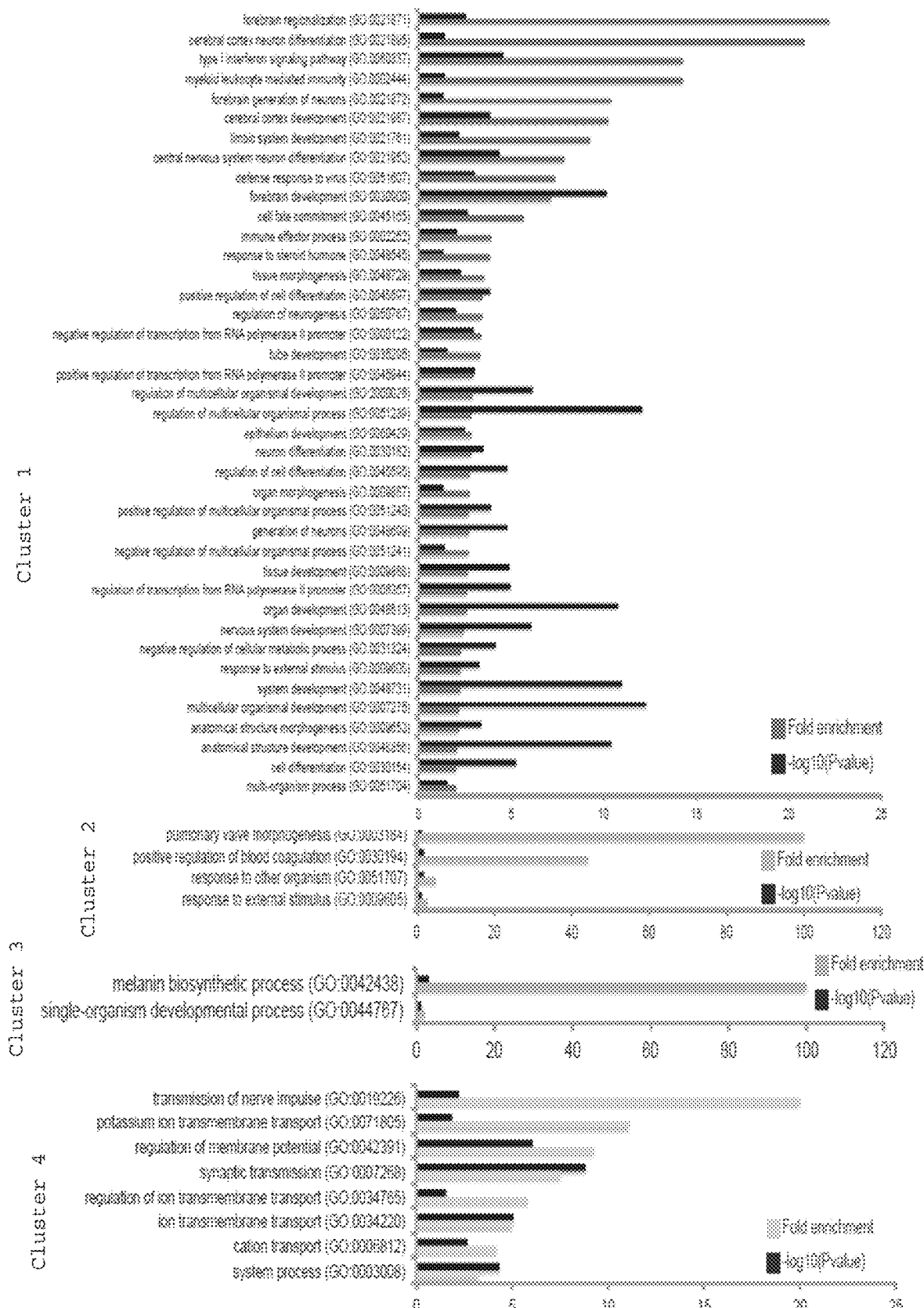
FIG. 17. GO terms in identified clusters of gene expression Fold enrichment and −log 10(P-value) of GO Biological Process terms for genes in 7 clusters identified by hierarchical clustering according to log 2fc value (FIG. 16b).

To further examine the effect of micropatterning and CHIR addition we analyzed gene expression at 20 and 60 days in three enCORs and three spherical organoids. 20 day enCORs were enriched for GO terms "neurological system" and "multicellular organismal processes", while other organ development like digestive tract, muscle, skeletal system and mesoderm were decreased (FIG. 16a). At 60 days, we observed GO term enrichment for nervous system development and transcription while digestive tract, heart, muscle skeletal system, and synaptic transmission were decreased. The decrease in synaptic genes at 60 days suggests a delay in neuronal maturation perhaps due to extended progenitor expansion upon CHIR addition. Hierarchical cluster analysis revealed several gene clusters displaying specific patterns of differential expression (FIG. 16b, 17). Cluster 1 was upregulated in 60 day enCORs and enriched for forebrain and cortical differentiation. Clusters 4 and 5 were increased or unchanged at 20 but decreased at 60 days and were enriched for nervous system development and synaptic transmission. Finally, Clusters 6 and 7 were decreased at 20 days and also decreased or unchanged at 60 days. They were enriched for more caudal expression such as spinal cord and hindbrain, consistent with the effect of micropatterning and CHIR addition on forebrain patterning.

We next assessed expression of specific germ layer or brain patterning markers (FIG. 18a, b). The pluripotency markers Oct4, Klf4, and Nanog were decreased in enCORs. Neuroectodermal markers appeared unchanged whereas mesendodermal markers such as Sox17, T (Brachyury), Mixl1, and Foxa2 were decreased. Furthermore, the forebrain marker Foxg1 was dramatically increased, whereas caudal markers such as En2, Gbx2 and Hox genes were decreased. Finally, dorsal forebrain markers such as Emx1, Tbr1 and Tbr2 were increased, while ventral forebrain markers were unchanged. These findings suggest a more rostral brain identity in enCORs.

We compared genes differentially expressed between 60 day spherical organoids and enCORs to gene expression in the human developing brain using Allen BrainSpan Atlas (FIG. 18c). enCORs most closely matched the dorsal forebrain identities of the human brain at early gestation, specifically 8-9 weeks postconception (FIG. 8d). Spherical organoids instead showed the highest correlation with more caudal regions, specifically the thalamus and cerebellum, and showed a broader correlation with later time points. These findings are consistent with the effect of micropatterning and CHIR addition on forebrain regional identity.

In addition to its proliferative role in neural progenitor expansion, Wnt signalling also plays a regional patterning role. Generally, Wnt is a dorsalizing factor in the CNS, and in the forebrain it is released from the hem, an organizing center that is a stimulator to dorsal cerebral cortex regionalization. Therefore, we tested whether the addition of CHIR during lateral expansion also affected regional identity. We performed staining for dorsal brain region identity, which revealed large Emx1+ regions (FIG. 2e), consistent with dorsal cortex. Furthermore, staining and quantification revealed that virtually all large regions stained positive for dorsal cortical markers Tbr1 and Tbr2 (FIG. 2f, g). This is in contrast to approximately 30% of large regions in spheroid organoids. These findings suggest that not only does the late CHIR treatment expand the neuroepithelium, but it also promotes reliable dorsal forebrain regionalization.

Example 10: Generation of Radial Cortical Plate with Dissolved ECM

The findings thus far suggest that micropatterning consistently produces cerebral organoids with large dorsal cortical regions, an important step towards modelling more subtle cortical phenotypes. This is improved by a combination with a short pulse of CHIR. However, we next sought to address the issue of neuronal organization and the lack of a cortical plate. We have previously described the generation of neurons of various layer identities, and recently we demonstrated the generation of these identities in a temporally controlled manner that mimics that seen in vivo. However, although excitatory neurons correctly migrate basally outward, once outside the progenitor zones they are randomly oriented and fail to re-establish the radially aligned morphology characteristic of the cortical plate. This reorientation is an important event in neuronal migration and the lack of this feature of cortical development makes it difficult to model neuronal migration defects in cerebral organoids.

Possibly migrating neurons make use of the basal process of radial glial neural stem cells as a scaffold for orientation and basal migration. Furthermore, because radial glia are epithelial in nature, the basal process contacts the basement membrane covering the surface of the brain. Since the basement membrane is generally thought to be generated by the overlying mesenchyme, a non-neural supportive tissue, we hypothesized that previous cerebral organoids might lack the basement membrane and therefore the contact site of radial glial processes, leading to disruption of the radial glial scaffold.

Figure 3:
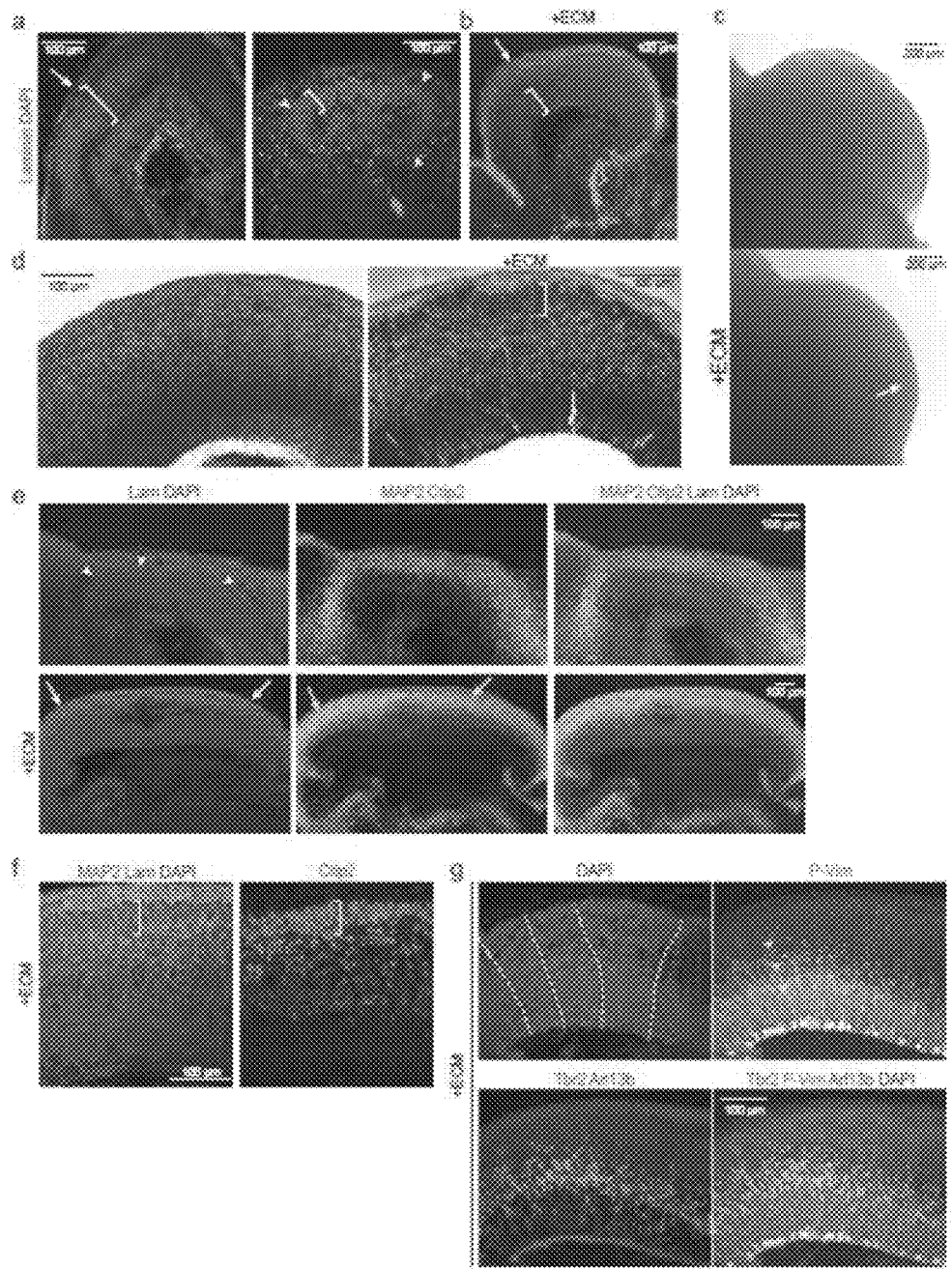
FIG. 3. a. Staining for the basement membrane component laminin (green) in spheroid organoids. Note the presence of the basement membrane surrounding the early neuroepithelium before the generation of neurons (first panel, arrow), whereas upon neuron generation only sparse labeling remains (arrowheads) adjacent to the ventricular zone (VZ, brackets) rather than over the surface of the organoid. b. Laminin staining of microfilament patterned organoids following treatment with dissolved extracellular matrix (ECM). Note the presence of a laminin-rich basement membrane covering the surface of the organoid (arrow) and outside both the VZ (bracket) and newly generated neurons. c. Bright field images organoids lacking dissolved ECM and microfilament patterned organoids with dissolved ECM showing a band of density upon addition of ECM (arrow) reminiscent of a dense cortical plate. d. Histological staining by haematoxylin and eosin reveals the presence of a radially oriented dense cortical plate (bracket) upon addition of dissolved ECM. e. Immunohistochemical staining for laminin and the neuronal markers MAP2 and Ctip2. Note the presence of remnant basement membrane without ECM addition (arrowheads), whereas upon addition of ECM a basement membrane (white arrows) forms outside the dense Ctip2+ cortical plate (yellow arrows). f. Higher magnification of immunostaining for Laminin, MAP2 and Ctip2 showing the radial orientation of neurons that have reached the cortical plate (brackets). g. Nuclear staining by DAPI reveals radially organized sections (dashed lines) while sparse staining for radial glial fibers with the marker of mitotic radial glia Phosphorylated vimentin reveals fibers that extend the width of the tissue (arrowheads) reminiscent of radial units.

In order to test this hypothesis, we performed immunohistochemical staining on cerebral organoids for the basement membrane component laminin. Surprisingly, we found that neuroepithelia that had not yet begun generating neurons displayed a well-formed laminin rich basement membrane covering the surface of the neuroepithelium (FIG. 3a). However, tissues with migrating cells outside the ventricular zone lacked a basement membrane, instead displaying punctate staining at the basal border of the ventricular zone. Interestingly, the staining pattern was consistent with residual basement membrane that had previously covered the basal surface of the neuroepithelium, suggesting breakdown of the membrane upon generation and basal migration of neurons.

We therefore sought to reconstitute and maintain the overlying basement membrane by providing exogenous extracellular matrix (ECM) components. Initially, brain organoids are embedded in an ECM rich gel (Matrigel) but within 1-2 weeks the organoids grow out of, or fall out of the gel droplets, leaving free floating brain tissue lacking the overlying ECM. We therefore tested the effect of dissolved Matrigel as a means to providing ECM components in the media. Remarkably, the tissues maintained a thick laminin rich basement membrane that was notably outside the migrating neurons (FIG. 3b), suggesting that it was not broken down by their generation and basal migration.

Figure 9:
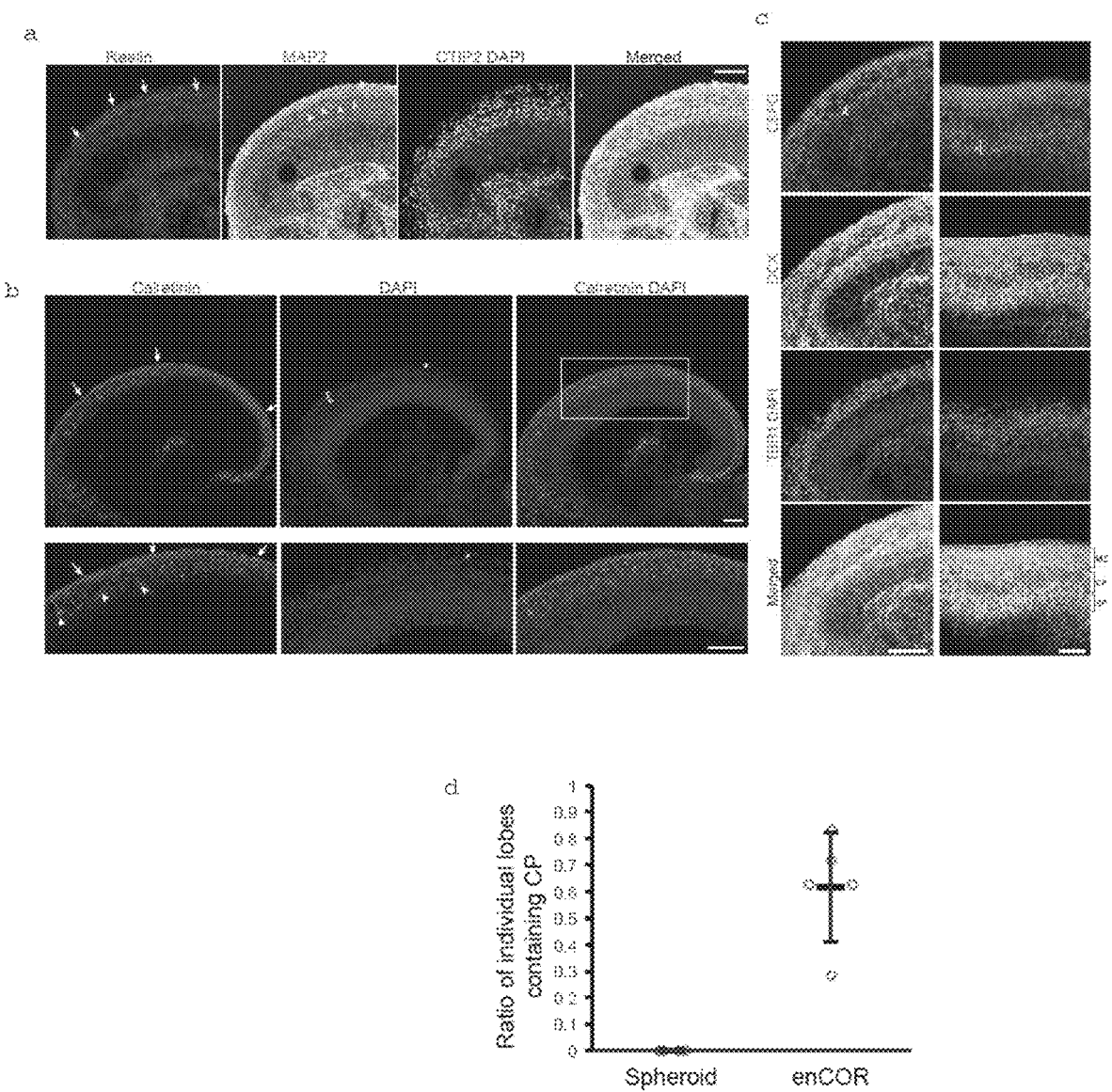
FIG. 9. a. Staining for Reelin in a dorsal cortical region early in CP formation (day-56 H9 enCOR). Several cells, which are strongly reactive for Reelin (arrows), localize outside the newly forming CP (arrowheads, recognizable by the lower intensity Map2 staining), consistent with Cajal-Retzius identity. Staining can also be seen more diffusely, consistent with its secreted role. b. Staining for calretinin, another marker of Cajal-Retzius cells, labels cells outside the newly forming CP (arrows) (day-53, H9 enCOR). Note the gradient of CP formation with more advanced CP to the left (bracket), and the initiation to the right (asterisk). Where the CP is further developed, one can also observe calretinin+ cells internal (arrowheads) to the CP, consistent with preplate splitting, and interneuron identity. c. Staining for chondroitin sulfate proteoglycan (CSPG) in day-68 H9 enCORs further demonstrates preplate splitting. Panels on the left show a less developed CP (yellow brackets) with the initiation of splitting and SP formation (white brackets), while panels on the right show a more developed CP with layers consistent with SP, CP, and MZ. Scale bars: 100 μm in all panels. d. Quantification of the mean ratio of individual lobes displaying a CP in H&E stained sections of day-60 H9 organoids. Individual lobes were identified by the presence of a ventricular space and radial VZ. CP was identified by the presence of a condensed band separated from the VZ by a cell-sparse zone. Each point is an independent batch of 2-3 organoids, each with several lobes of brain tissue. n=4 independent batches of 12 spheroids, n=5 independent batches of 12 enCORs. Error bars are standard deviation.

We allowed the microfilament patterned brain organoids to develop in the presence of dissolved ECM for 20 days and examined their morphology. Bright field imaging revealed a band of density in cortical regions that was absent in organoids lacking dissolved ECM (FIG. 3c). Subsequent sectioning and histological staining revealed a radialized basal layer consistent with cortical plate morphology (FIG. 3d). Indeed, immunohistochemical staining revealed it was positive for the neural markers Ctip2, Map2, and DCX, with a band of lower Map2 staining in cell bodies that is typical of the cortical plate in vivo (FIG. 3e, f). Bright field imaging revealed a band of density in cortical regions that was absent in organoids lacking dissolved ECM (FIG. 3c). Quantification of the presence of a cortical plate revealed reproducible formation in five independent batches of enCORs while a cortical plate was never observed in spheroids (FIG. 9d).

Since the maintenance of a basement membrane led to establishment of an organized cortical plate, we hypothesized that this may be due to the presence of a radial glial scaffold. We therefore performed staining for individual radial glia and their processes by staining for phosph-vimentin, a cytoplasmic marker of dividing radial glia. We could identify long basal processes that extended the length of the cortical wall (FIG. 3g). Notably, nuclear staining alone revealed linear units of radial glia and neurons aligned in a manner reminiscent of radial units, suggesting an organized radial glial scaffold.

To further examine the role of Matrigel and its role in formation of a cortical plate (CP), we instead performed treatment with the matrix metalloprotease inhibitor GM6001 to test whether inhibition of ECM breakdown is sufficient for CP formation. Continuous treatment beginning at day 30 did not result in CP formation by 60 days (FIG. 19a), suggesting that it is not simply breakdown of the initial basement membrane that inhibits CP formation in the spherical organoid method, but also a failure to maintain and expand the basement membrane with tissue growth, a hurdle overcome by addition of dissolved Matrigel. We next tested whether laminin alone or in combination with entactin would be sufficient to recapitulate the effect of dissolved Matrigel. These treatments did not recapitulate the extent of CP formation seen with Matrigel (FIG. 19b), suggesting other components of this complex ECM are important for basement membrane maintenance.

Example 11: Comparisons and Further Characteristics of Micropatterned EB Based Organoids (enCORs)

Figure 19:
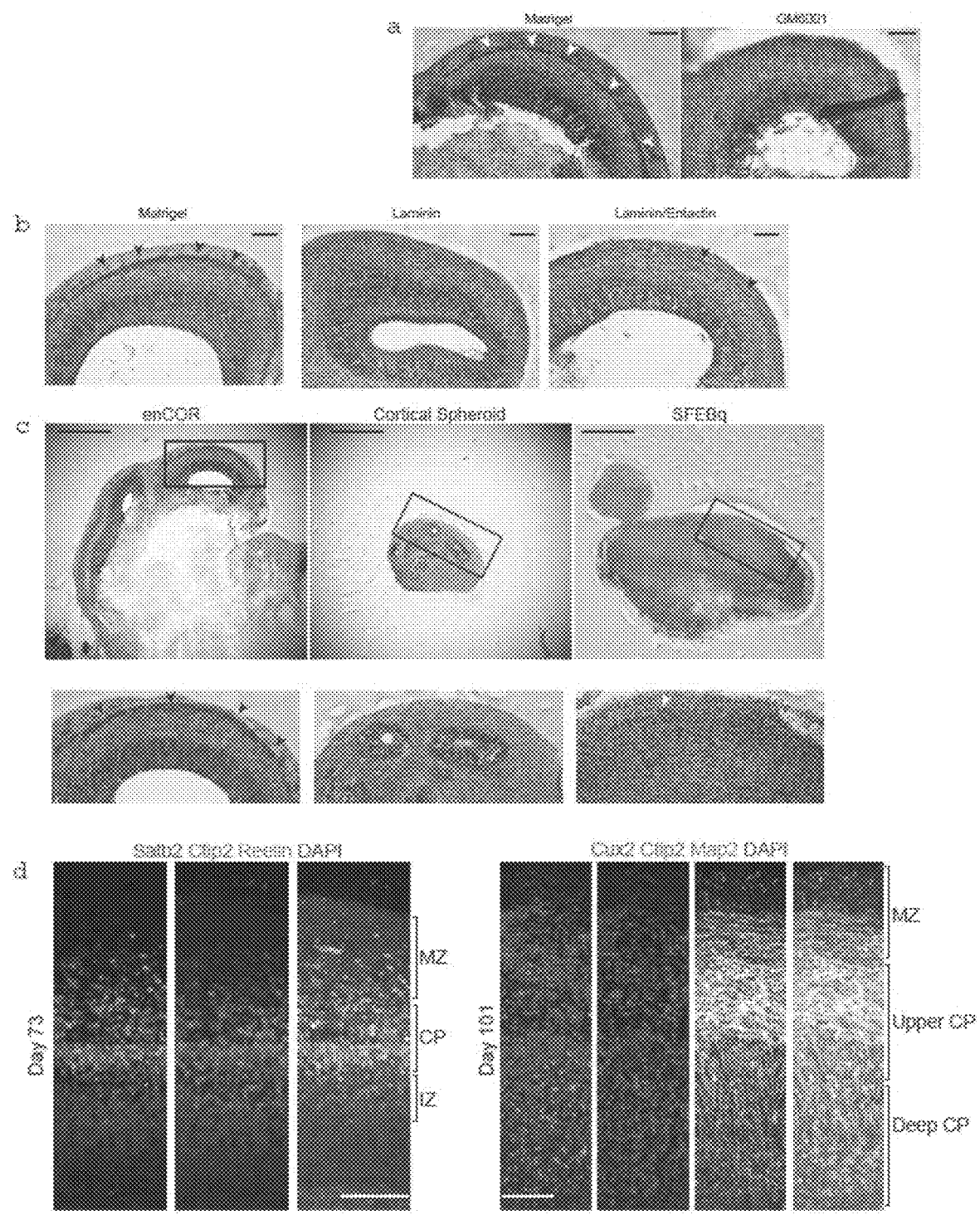
FIG. 19. enCORs with ECM addition display organized cortical plate a. H&E staining of 60-day H9 enCORs with dissolved Matrigel show a dense band consistent with CP, whereas enCORs instead treated from day 30 with the matrix metalloprotease inhibitor GM6001 show no signs of CP formation. b. H&E staining of 60-day H9 enCORs with dissolved Matrigel compared with dissolved laminin or dissolved laminin/entactin complex. Note the presence of a dense CP band with Matrigel, while laminin alone displays no evidence of CP formation and laminin/entactin develops only a faint band of cells. c. H&E staining of H9 enCOR, H9 cortical spheroid generated according to Pasca et al.25 and iPSC SFEBq generated according to Kadoshima et al.24, each at 60-days of development. Note the dense CP band (black arrowheads) with the enCOR method and the overall larger size as well as presence of larger lobes surrounding fluid-filled ventricle-like spaces. The SFEBq method gives rise to a marginally condensed band of neurons (white arrowhead). Lower panels are higher magnifications of the boxed regions. d. Staining for neuronal subtypes in developing CP in H9 enCORs at two time points reveals the progressive separation of upper layer (Satb2+ and Cux2+) which labels a broad population, and deep layer (Ctip2+) neurons which label neurons in deeper regions of the CP. Note the progressive thickening of the radially organized CP, and the evident layers exhibiting transitioning organization of neuronal processes (Map2 staining). Scale bars: 200 μm in FIG. 3c., 100 um in FIG. 3f., FIGS. 19a., b., and d., and 500 μm in FIG. 19 c.

We compared enCORs with cortical spheroids and SFEBq organoids described by Kadoshima et al., Proc. Natl. Acad. Sci. U.S.A. 110, 20284-20289 (2013). Neither cortical spheroids nor SFEBq organoids displayed a clear, radially organized CP as seen in enCORs (FIG. 19c). These data suggest that in enCORs the events leading to proper neuronal organization may be more similar to in vivo development as compared to cortical spheroids and SFEBq organoids.

CP establishment in vivo depends upon early pioneer neurons of the preplate, which secrete Reelin to attract subsequent neurons to migrate into and split the preplate into the marginal zone (MZ) and subplate (SP). We therefore tested whether enCORs exhibited Reelin expressing neurons, also called Cajal-Retzius cells, by staining for Reelin and calretinin. Staining for Reelin revealed strongly reactive cells in the most superficial regions, as well as more dispersed signal indicative of the fact that Reelin is a secreted factor (FIG. 9a). Furthermore, calretinin staining revealed neurons in superficial regions as well as just inside the newly forming CP (FIG. 9b), a pattern typical of preplate splitting in vivo. Staining for chondroitin sulfate proteoglycan (CSPG) further revealed splitting and establishment of MZ and SP during early CP condensation (FIG. 9c). This separation was more pronounced with more developed, thicker CP. The CP itself widened over time and even displayed features of early cortical layering (FIG. 19d).

Figure 10:
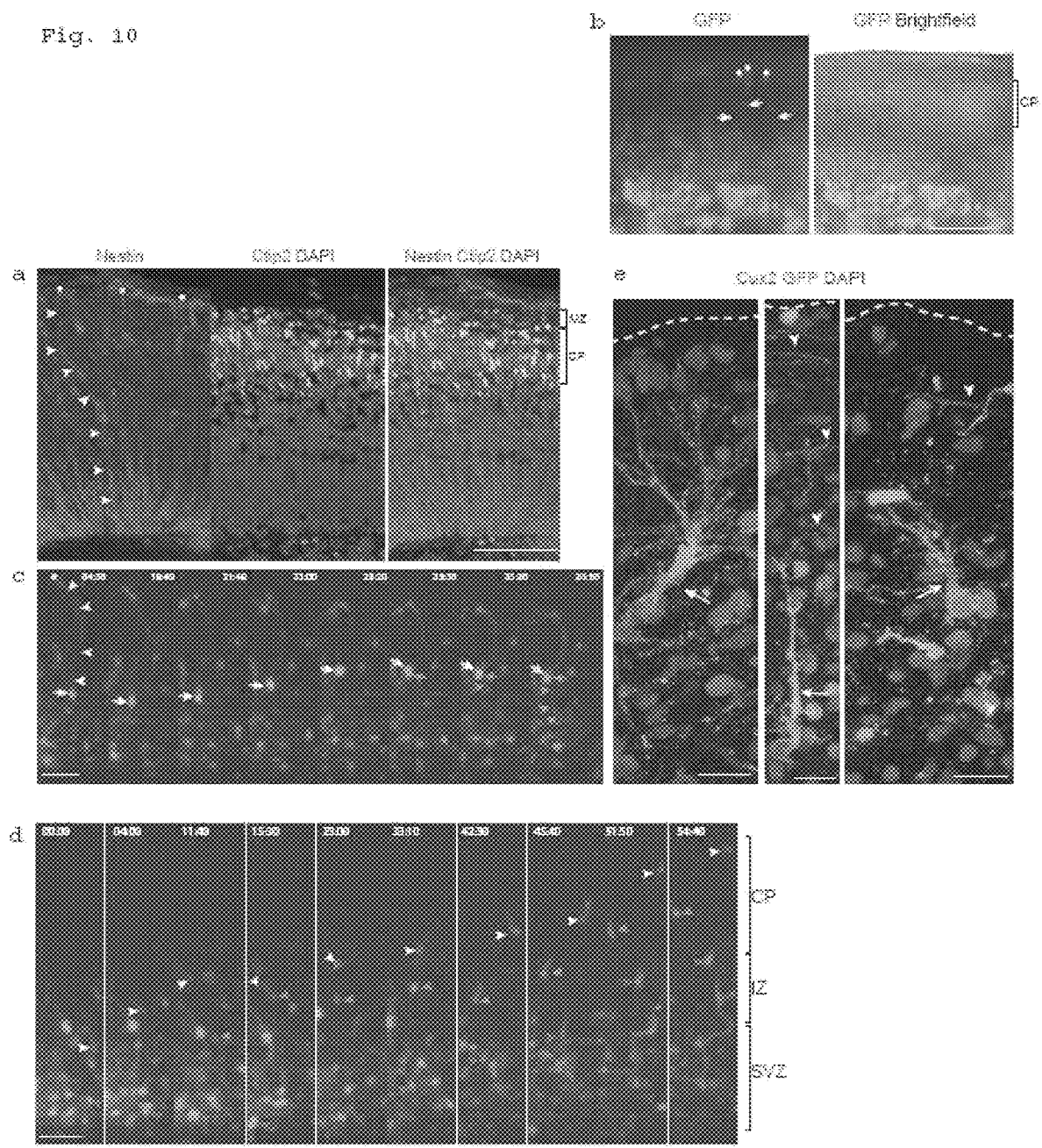
FIG. 10. enCORs display radial units and radial neuronal migration. a. Nestin staining for radial glia in day-70 H1 enCORs reveals long basal processes (arrowheads) that terminate with end feet at the surface of the organoid (asterisks) outside the CP and MZ. b. Electroporation of the VZ of a 64-day H9 enCOR with a GFP construct and vibratome sectioning the next day reveals individual RG basal processes (arrows) that extend to the outer surface (asterisks). c. Live imaging of an outer/basal RG (arrow marks the cell body) in a H1 enCOR electroporated with GFP on day 63, followed by vibratome sectioning four days later and live imaging 24-hours later. Note the long basal process (arrowheads) and endfoot (asterisk) as well as a division event including mitotic somal translocation beginning at 21:40. The newly generated daughter cell (blue arrow) then extends a process apically (blue arrowheads). Time stamp is hours:minutes. d. Live imaging of migration of several neurons (arrowheads) in the same sample as d., displaying typical radial migration including transient stalling with multipolar morphology (for example white arrowhead 11:40 to 23:00). Time stamp is hours:minutes. e. Individual neurons labeled by electroporation of an H9 enCOR at day 64 with an integrating farnesylated GFP construct to allow for long-term labeling and analysis after 36 days. Note the primary dendrite extending from the cell body (arrows) toward the outer surface (oriented up in all images), as well as many parallel fibers (arrowheads) in the outer cell sparse MZ. Scale bars: 100 μm in FIG. 3$g$., FIG. 10$a$., $b$., 50 μm in $c$., $d$., 20 μm in e.
Figure 20:
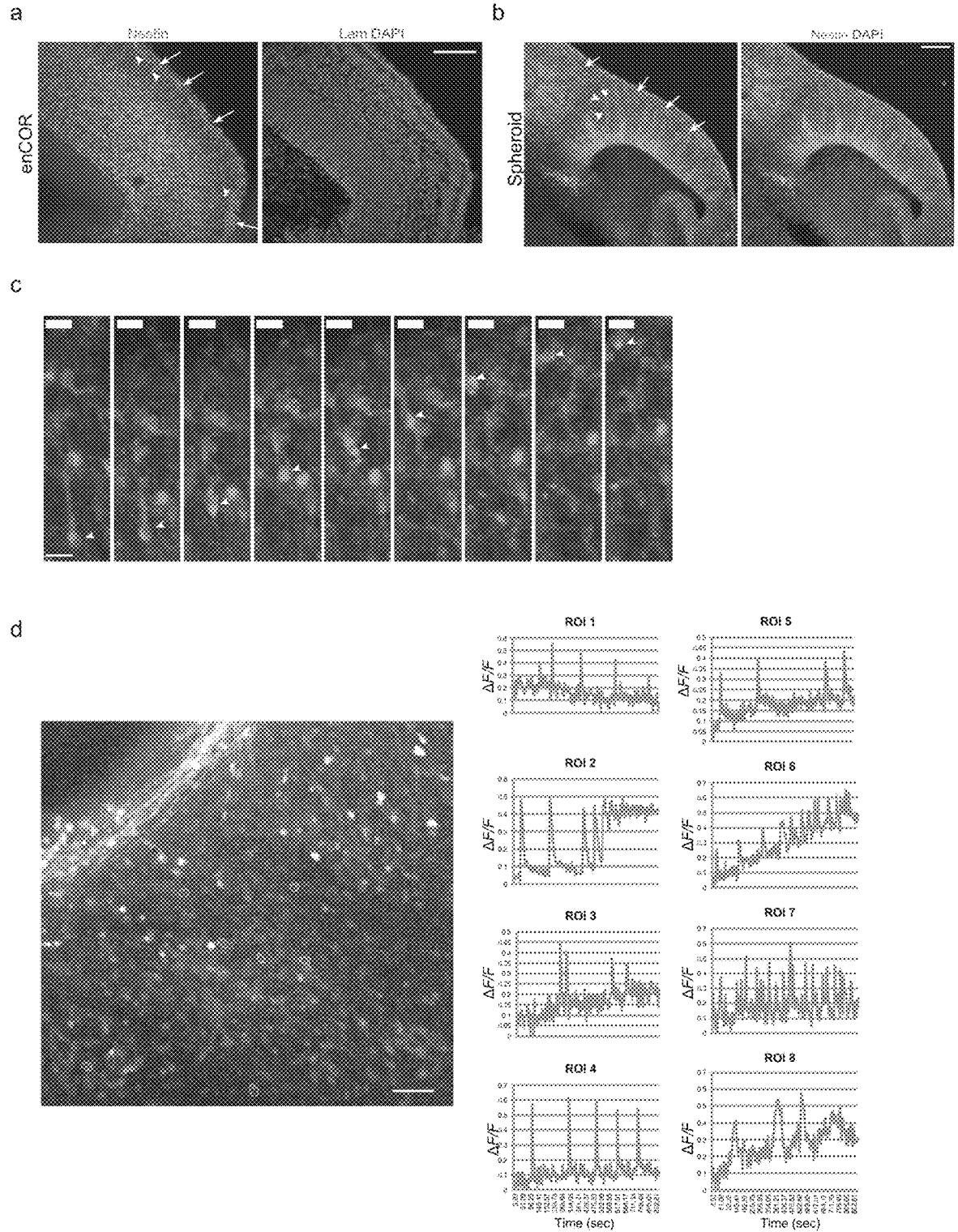
FIG. 20. Slice culture and live imaging in enCORs enables visualization of neuronal migration and activity. a. Nestin staining reveals basal processes (arrowheads) with end feet that terminate at the laminin positive basement membrane (arrows) in a 60-day H9 enCOR. b. Nestin staining in 60-day H9 spheroid reweals the presence of radial glial processes that show disorganization outside the ventricular zone (arrowheads) and terminal end feet within the tissue (arrows). c. Frames from live imaging of a membrane targeted farnesyl-GFP labeled neuron (arrowhead) showing radial migration into the CP. d. A false color heatmap frame of live imaging with the calcium dye Fluo-4 and single cell tracings of the indicated cells, labeled regions of interest (ROI), as measured by change in relative fluorescence (ΔF/F=(mean grey value−minimum grey value)/ minimum grey value) showing spontaneous calcium surges. Scale bars: 100 µm in a. and b., 20 µm in c., 50 µm in d.

The basal process of radial glial cells, which contacts the basement membrane covering the surface of the brain, acts as a scaffold for migration and orientation of neurons to allow for formation of the CP and positioning into radial units. Nuclear staining in cortical regions of enCORs which had been sectioned evenly perpendicular to the apicobasal axis revealed linear units of radial glia and neurons aligned in a manner reminiscent of radial units (FIG. 3a), a characteristic architecture not previously recapitulated in vitro. Furthermore, staining for phospho-vimentin, a cytoplasmic marker of dividing radial glia revealed long basal processes extending the length of the cortical wall. These basal processes were also evident upon staining for Nestin, a cytoplasmic marker of radial glia, which revealed processes with end feet that terminated on the outer surface (FIG. 10a, FIG. 20a). In contrast, spherical organoids displayed disorganized radial glial processes with terminating end feet at various locations within the tissue (FIG. 20b).

In order to label individual cells for live imaging and morphological analyses, we next established combined electroporation and slice culture in organoids, an approach not previously applied to these types of in vitro cultures. We electroporated a GFP construct into the VZ of individual cortical lobes followed by vibratome sectioning and culture at the air-liquid interface. This allowed for marking individual radial glia, further demonstrating the long basal processes terminating superficial to the CP (FIG. 10b).

Long term live imaging of electroporated slices revealed various cell behaviors including divisions of outer radial glia (oRG), also called basal radial glia (FIG. 10c), which displayed mitotic somal translocation, a feature typical of oRGs in vivo. Furthermore, live imaging of labelled neurons revealed typical radial migration with saltatory movements and transient acquisition of multipolar morphology before reestablishment of radial orientation and migration into the CP (FIG. 10d, FIG. 20c). Establishment of labelling and long term live imaging of slice cultures in this manner thus provides a useful tool for examination of neuronal migration and progenitor division in a human model system.

Electroporation of a membrane targeted GFP allowed for examination of morphology of single neurons in more developed organoids. This revealed complex dendritic morphologies and neurons with a primary dendrite typical of the pyramidal morphology of cortical neurons (FIG. 10e). Furthermore, these neurons were oriented toward the MZ on the outer surface of the organoid where parallel fibers could frequently be seen. Finally, we performed calcium staining and live imaging on slice cultures, which revealed spontaneous calcium surges suggestive of neuronal activity (FIG. 9d). These data point to proper positioning and maturation of cortical neurons in enCORs.

Example 12: Use of Organoids as Disorder Model and Rescue Screen System

Because enCORs establish a CP and exhibit characteristic neuronal migration in a manner not previously recapitulated in vivo, this system could provide a useful tool for the investigation of human disorders of neuronal migration or positioning. In order to test this possibility, we sought to model fetal alcohol syndrome (FAS), a leading preventable cause of intellectual disability affecting approximately 0.5-2 in 1000 births in the United States. FAS is characterized by neurodevelopmental abnormalities including microcephaly, thin or absent corpus callosum, and neuronal migration defects such as polymicrogyria, heterotopia, and focal lissencephaly.

We treated organoids with three concentrations of ethanol to determine the phenotypic range as well as to test the appropriate concentration considering the volatility of ethanol. We performed treatments every 3-4 days for two weeks by adding the appropriate volume at media changes. Measurement of the resultant ethanol concentration in the media revealed that for all doses tested there was a progressive decrease in concentration over time and even the initial concentration was substantially lower due to high volatility (FIG. 21a). Furthermore, while the higher dose of 150 mM ethanol was initially outside the physiological range, it quickly dropped to approximately 60 mM within a day, a concentration equivalent to a blood alcohol content of 0.27% by volume. A similar trend was seen with the lower doses of 87 mM and 43.5 mM. The inconstant nature of the treatment, with transient peak concentration every 3-4 days upon media change, thus reflects a scenario that might be seen with binge drinking.

Figure 11:
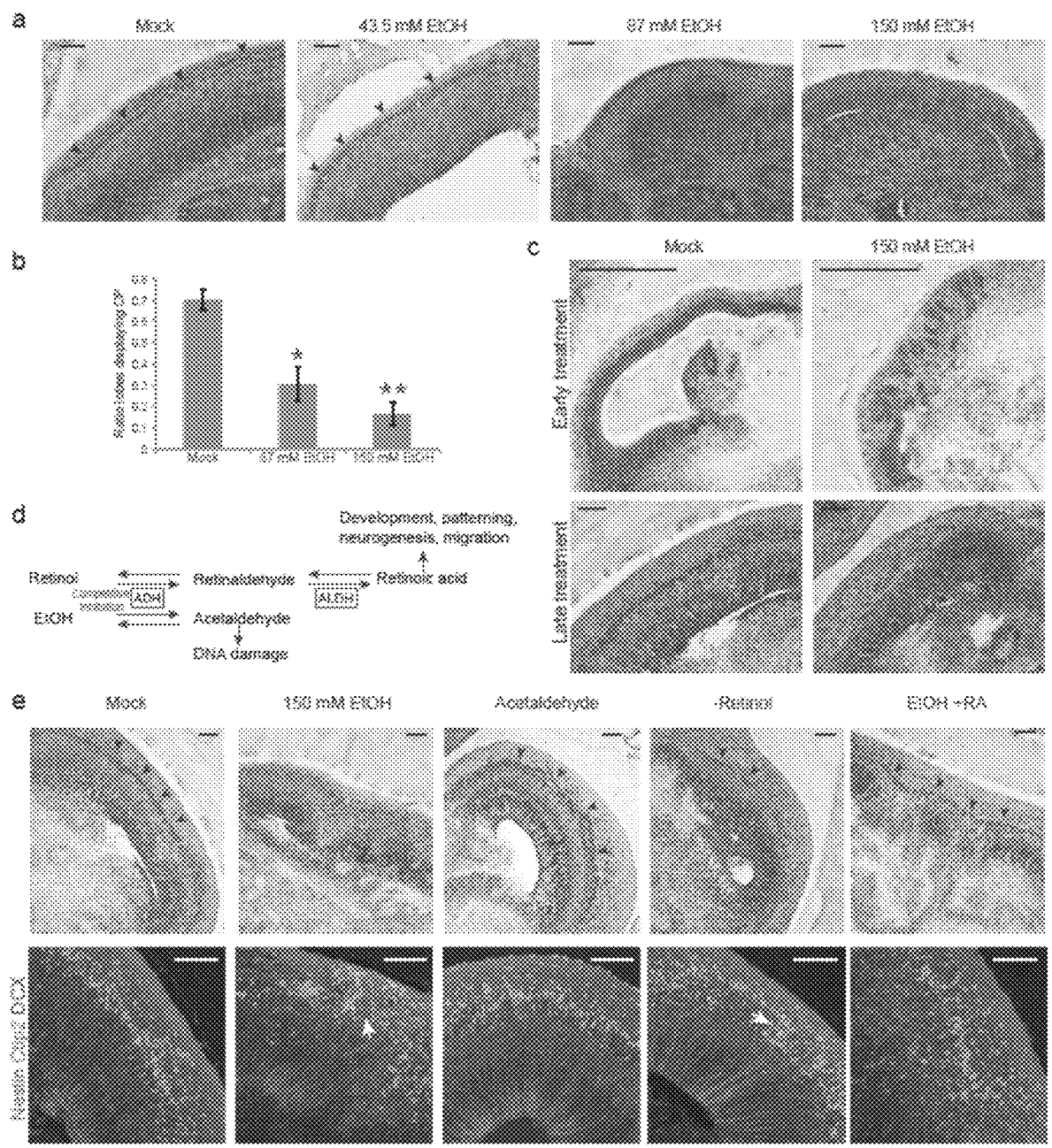
FIG. 11. Ethanol treatment leads to defects in cortical plate formation which is phenocopied by omitting retinols a. H&E histology of 70-day H1 enCORs treated beginning on day 56 with three doses of ethanol or water as mock control four times over the course of two weeks reveals the loss of the radial cortical plate (arrowheads) in higher ethanol treatments (87 mM and 150 mM) compared with control. These higher concentrations also display smaller ventricular surfaces. b. Quantification of the mean ratio of cortical lobes containing a dense, radial band, recognizable on H&E staining, consistent with cortical plate reveals a reduction in 87 mM and 150 mM ethanol treated tissues. Error bars are SEM. *$P<0.05$, **$P<1.0e-6$ Student's t-test, n=13 organoids from five batches (4 H9, 1 H1) for control, 4 organoids from two batches (1 H9, 1 H1) for 87 mM EtOH, and 12 organoids from four batches (3 H9, 1 H1) for 150 mM EtOH. All treatments were performed beginning at day 56 with analysis at day 70. c. H&E stained sections of enCORs treated with 150 mM EtOH or water mock before the onset of CP formation (labeled early, iPSC enCORS treated beginning 11 days after ECM addition before evidence of CP on brightfield, analyzed day 70) reveals a more dramatic effect on VZ morphology and continuity compared with organoids treated after the onset of CP formation (labeled late, H9 enCORs treated beginning 16 days after ECM addition, analyzed day 70). d. Schematic of the metabolic pathways of retinol and ethanol and potential for competitive inhibition. e. H&E histology and immunohistochemical staining for nestin to mark radial processes, and Ctip2 which marks the CP, in mock and treated H9 enCORs at day 70, after 2 weeks treatment. Note the intact CP (arrowheads) in acetaldehyde treated samples, whereas ethanol treated lack a well-developed CP and samples with retinol also display malformed CP. The combination of retinoic acid treatment with ethanol partially rescues the phenotype with the formation of a more discrete condensed CP, but still displaying defects in VZ continuity. Nestin staining reveals bundles of basal processes that extend beyond the main neuronal population and into external heterotopias upon ethanol treatment (arrows). DCX (Doublecortin) marks neurons. This disorganization is also evident in the absence of retinols. Scale bars: 100 μm in a., c.—bottom panel, e., 500 μm in c.—top panel.

We next examined histological preparations of enCORs treated with the three ethanol doses, which revealed a striking effect on CP formation that was dose dependent with the higher dose of 150 mM completely lacking a CP whereas the lowest dose of 43.5 mM was completely normal (FIG. 11a). We quantified the number of tissues displaying a recognizable CP in control and the two higher doses where a phenotype was evident, which further demonstrated the dose responsiveness (FIG. 11b).

Notably, 150 mM treatment also displayed defects in the VZ with less continuity and smaller ventricular surfaces, a potential feature consistent with microcephaly seen in FAS. To investigate this effect further, we also tested a very high concentration of 300 mM, which resulted in highly disorganized ventricular zones with a large number of abnormally located neurons, having failed to migrate basally outward (FIG. 21b). Furthermore, we tested timing of ethanol challenge by treating enCORs before CP formation when lateral expansion was still occurring (FIG. 11c). These tissues displayed dramatic disruption of the VZ and a lack of large continuous lobes with large ventricles. Importantly, while the effect on CP formation and neuronal migration could not be modelled in spheroids, the effects on VZ continuity were evident (FIG. 21c). Finally, these effects were not simply due to an effect on cell survival as TUNEL staining did not reveal a noticeable increase in apoptotic/necrotic cells in any of the three treatment concentrations (FIG. 21d).

While the mechanism of action of ethanol teratogenicity in brain development is not yet known, several studies have pointed to the possibility that ethanol may interfere with metabolism of vitamin A to its active form, retinoic acid, through competitive inhibition of alcohol dehydrogenases that act on alcohols including ethanol and retinol (FIG. 11d). Interestingly, there are many members of this class of enzyme, several of which are expressed in enCORs (FIG. 21e). Another possibility, however, is that the acetaldehyde produced from ethanol metabolism acts through its DNA damaging properties to disrupt brain development. We sought to test these two possibilities by performing treatments with metabolites of the retinol and ethanol metabolic pathways.

We performed a combination of histological and immunohistochemical staining for neurons and nestin in order to examine the effect on the radial scaffold and neuronal positioning. Ethanol treatment resulted in disruption of the CP with overmigration of neurons and abnormal accumulations at the surface of the organoid (FIG. 11e) consistent with the formation of external heterotopias, previously described in models of FAS. This was accompanied by radial processes that extended beyond the main neuronal population and into the ectopic region. In contrast, treatment with acetaldehyde did not result in noticeable defects in either CP formation or VZ morphology (FIG. 11e), suggesting the effects of ethanol are not through its downstream metabolite.

In order to test for potential competition with vitamin A metabolism and retinoic acid production, we tested whether a complete absence of vitamin A (retinol) could recapitulate the effects, by omitting vitamin A from the media for the same period that we performed ethanol treatment. Similar to ethanol treatment, a lack of retinol resulted in disorganized CP and overmigration with abnormal clusters of nestin positive basal processes (FIG. 11e). Furthermore, treatment with the downstream active product, retinoic acid, along with ethanol, led to a partial rescue with a notably intact CP. However, there were still defects in the VZ suggesting this aspect of the phenotype is not through competitive inhibition of retinol metabolism. These data support that retinoids are required for proper neuronal migration and formation of a CP, and further suggest the teratogenic effects of ethanol may be through interference with this pathway.

The remarkable self-organization and ability to generate the full repertoire of organ cell types have made organoids an important new model system. However, the high variability and difficulties modelling later tissue architecture has meant that subtle defects are difficult to discern. To overcome this, we have combined organoids with bioengineering using a novel microscale internal scaffold. This method enables the study of neuronal migration disorders, and we examine such defects associated with FAS as a proof of principle. Finally, we demonstrate interaction with retinol metabolism as a mechanism of ethanol induced CP defects and heterotopias.

The invention claimed is:

1. A fiber-supported multicellular aggregation of neural lineage with neuronal differentiated cells wherein cells are arranged on a fibrous structured support, wherein said support is a biocompatible polymer that is not a biopolymer or wherein said fibrous structured support is a protein, and said support consists of 1 to 50 fibers, and wherein said aggregate contains cells at different stages of differentiation, including polar cells, the polar cells having a uniform orientation; and wherein said multicellular aggregation is having a size of at least 50 μm.

2. The aggregation of claim 1, comprising between 8000 and 100 Million cells.

3. A method of generating an artificial neuronal tissue culture, comprising:
   providing a fiber-supported multicellular aggregation of neural lineage as defined in claim 1;
   culturing said elongated or fiber-supported multicellular aggregation in a three dimensional matrix, wherein said cells are allowed to differentiate, thereby expanding said cells; and
   culturing said expanded cells of step p) in a suspension culture.

4. The method of claim 3, further comprising step r) adding dissolved material of a three dimensional matrix to said suspension culture, whereby the dissolved material adheres to the culture and forms a matrix.

5. The method of claim 4, wherein the dissolved material of a three dimensional matrix is dissolved extracellular matrix.

6. A method of generating an artificial neuronal tissue culture, comprising:
   providing multicellular aggregation of neural lineage as defined in claim 1,
   culturing said multicellular aggregation in a three dimensional matrix,
   wherein said cells are allowed to differentiate, thereby expanding said cells, culturing said expanded cells of step v) in a suspension culture; and adding dissolved material of a three dimensional matrix to said suspension culture, whereby the dissolved material adheres to the culture and forms a matrix, wherein the dissolved material of a three dimensional matrix is dissolved extracellular matrix.

7. The method of claim 3, wherein the three dimensional matrix is a gel.

8. An artificial neuronal tissue culture comprising a fiber-supported multicellular aggregation of claim 1.

9. An artificial neuronal tissue culture comprising a fiber-supported multicellular aggregation of claim 1 and comprising a radially organized cortical plate; wherein said tissue culture is in vitro grown from an aggregate of cells and/or is not a culture of an in vivo developed brain or a tissue sample thereof.

10. The tissue culture of claim 9, comprising a basement membrane comprising laminin; a basement membrane covering a basal surface of neuroepithelium; a basement membrane outside of migrating neurons; a radially organized cortical plate comprising the expression markers Ctip2, Map2, DCX, or any combination thereof, especially Ctip2, Map2 and DCX.

11. The tissue culture of claim 9, further comprising Map2 or radial glia.

12. The tissue culture of claim 9, comprising linear units of radial glia and neurons.

13. The method of testing or screening a candidate drug for developmental effects, especially for congenital disorder effects, comprising administering a candidate drug to an artificial culture according to claim 9, and determining an activity of interest of the cells of said culture and comparing said activity to an activity of cells to the culture without administering said candidate drug, wherein a differential activity indicates a developmental effect.

14. The method of claim 3, wherein a kit is used in the method, said kit comprises i) a solid support of rod-shaped or lattice-shaped or fibrous structure, and said support has a length of 20 μm to 20 mm and a diameter of 1 μm to 60 μm, and comprises ii) a three-dimensional matrix and/or an extracellular matrix or any component thereof selected from collagen, laminin, entactin, and heparin-sulfated proteoglycan or any combination thereof.

15. The method of claim 14, wherein the kit comprises an extracellular matrix from the Engelbreth-Holm-Swarm tumor or Matrigel.

16. The method of claim 14, wherein the kit further comprises vitamin C; vitamin A, 2-mercaptoethanol; bFGF; ROCK inhibitor; insulin; a GSK3beta inhibitor; a Wnt activator, preferably CHIR 99021; an antibacterial agent; a SMAD inhibitor; a retinoid; or any combination thereof.

17. The method of claim 14, wherein the three dimensional matrix is a gel.

18. The method of claim 3, wherein a kit is used in the method, said kit comprises a rod-shaped or lattice-shaped or fibrous structured support and said support has a length of 20 μm to 20 mm and a diameter of 1 μm to 60, and at least a compound selected from vitamin C; vitamin A, 2-mercaptoethanol; bFGF; ROCK inhibitor; insulin; a GSK3beta inhibitor; a Wnt activator; an antibacterial agent; a SMAD inhibitor; a retinoid; or any combination thereof.

19. An elongated multicellular aggregation of neural lineage with neuronal differentiated cells wherein cells are arranged in an oblong or longish arrangement with an aspect ratio of a prolate dimension to a perpendicular dimension of at least 2:1, and wherein the cells are arranged on a support consisting of 1 to 50 fibers; including polar cells, the polar cells having a uniform orientation; and wherein said multicellular aggregation is having a size of at least 50 μm.

20. The elongated multicellular aggregation of claim 19 obtainable by the method of generating multicellular aggregation of neural lineage with neuronal differentiated cells comprising the steps of:

a) providing a plurality of pluripotent or non-human totipotent cells (i) that are located in an oblong or longish arrangement adhered to a support, said support has a length of 20 μm to 20 mm and a diameter of 1 μm to 60 μm, wherein said support is a biocompatible polymer that is not a biopolymer or wherein said support is a protein, or (ii) that are arranged on a fibrous structured support, and said support has a length of 20 μm to 20 mm and a diameter of 1 μm to 60 μm, wherein said fibrous structured support is a biocompatible polymer that is not a biopolymer or wherein said fibrous structured support is a protein; and b) letting said cells grow and differentiate in said arrangement, wherein said cells form intercellular bonds and adhere to each other;

wherein said cells are stimulated to differentiate by a contacting the cells with a neuronal growth or differentiation factor; and wherein in said method said support is dissolved or bio-resorbed after step b).

21. The aggregation of claim 1, comprising polarized neuroectoderm.

22. The aggregation of claim 19, comprising polarized neuroectoderm.

23. The fiber-supported multicellular aggregation of claim 1, wherein a fiber has a length of 20 μm to 20 mm and/or a diameter of 1 μm to 60 μm.

24. The elongated multicellular aggregation of claim 19, wherein a fiber has a length of 20 μm to 20 mm and/or a diameter of 1 μm to 60 μm.

25. The aggregation of claim 1, having a size of between 50 μm to 40 mm.

* * * * *